United States Patent
Boswell et al.

(10) Patent No.: US 10,959,918 B2
(45) Date of Patent: Mar. 30, 2021

(54) FILMS INCLUDING A WATER-SOLUBLE LAYER AND A VAPOR-DEPOSITED COATING

(71) Applicant: The Procter & Gamble Company, Cincinnati, OH (US)

(72) Inventors: Emily Charlotte Boswell, Cincinnati, OH (US); Elizabeth Anne Wilder, West Chester, OH (US); Rachit Malik, Hillsboro, OR (US); Colin Wiliam McConnell, Loveland, OH (US); Vesselin Nikolov Shanov, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 301 days.

(21) Appl. No.: 16/015,644

(22) Filed: Jun. 22, 2018

(65) Prior Publication Data

US 2018/0369079 A1 Dec. 27, 2018

Related U.S. Application Data

(60) Provisional application No. 62/523,290, filed on Jun. 22, 2017, provisional application No. 62/523,298, filed on Jun. 22, 2017, provisional application No. 62/523,303, filed on Jun. 22, 2017, provisional application No. 62/523,295, filed on Jun. 22, 2017.

(51) Int. Cl.

| | | |
|---|---|---|
| *A61K 8/02* | (2006.01) | |
| *A61Q 19/08* | (2006.01) | |
| *B05D 1/00* | (2006.01) | |
| *C23C 16/40* | (2006.01) | |
| *C23C 16/515* | (2006.01) | |
| *B05D 7/00* | (2006.01) | |
| *B05D 7/04* | (2006.01) | |
| *A61Q 19/00* | (2006.01) | |
| *A61K 8/67* | (2006.01) | |
| *A61K 8/49* | (2006.01) | |
| *A61K 8/81* | (2006.01) | |
| *A61K 8/34* | (2006.01) | |

(52) U.S. Cl.
CPC .......... *A61K 8/0208* (2013.01); *A61K 8/0212* (2013.01); *A61K 8/345* (2013.01); *A61K 8/498* (2013.01); *A61K 8/673* (2013.01); *A61K 8/675* (2013.01); *A61K 8/8194* (2013.01); *A61Q 19/00* (2013.01); *A61Q 19/08* (2013.01); *B05D 1/60* (2013.01); *B05D 7/04* (2013.01); *B05D 7/54* (2013.01); *B05D 7/58* (2013.01); *C23C 16/401* (2013.01); *C23C 16/403* (2013.01); *C23C 16/515* (2013.01); *A61K 2800/10* (2013.01); *A61K 2800/30* (2013.01); *A61K 2800/81* (2013.01)

(58) Field of Classification Search
None
See application file for complete search history.

(56) References Cited

U.S. PATENT DOCUMENTS

| | | |
|---|---|---|
| 3,155,034 A | 11/1964 | Reinke |
| 3,482,300 A | 12/1969 | Reinke |
| 3,696,741 A | 10/1972 | Reinke |
| 3,759,799 A | 9/1973 | Reinke |
| 3,759,800 A | 9/1973 | Reinke |
| 4,341,209 A | 7/1982 | Schaar |
| 4,377,616 A | 3/1983 | Ashcraft et al. |
| 4,472,328 A | 9/1984 | Sugimoto et al. |
| 4,519,538 A | 5/1985 | Omichi |
| 4,578,297 A | 3/1986 | Duncan |
| 4,649,186 A | 3/1987 | Jenkins et al. |
| 4,699,792 A | 10/1987 | Nick et al. |
| 4,711,781 A | 12/1987 | Nick et al. |
| 4,725,439 A | 2/1988 | Campbell et al. |
| 4,743,249 A | 5/1988 | Loveland |
| 4,773,408 A | 9/1988 | Cilento et al. |
| 4,781,294 A | 11/1988 | Croce |
| 5,051,259 A | 9/1991 | Olsen et al. |
| 5,123,900 A | 6/1992 | Wick |
| 5,132,115 A | 7/1992 | Wolter et al. |
| 5,180,626 A | 1/1993 | Ishibashi et al. |
| 5,262,165 A | 11/1993 | Govil et al. |
| 5,387,450 A | 2/1995 | Stewart |
| 5,455,043 A | 10/1995 | Fischel-Ghodsian |
| 5,476,664 A | 12/1995 | Robinson et al. |
| 5,503,844 A | 4/1996 | Kwiatek et al. |

(Continued)

FOREIGN PATENT DOCUMENTS

| | | |
|---|---|---|
| EP | 0238200 A2 | 9/1987 |
| EP | 0904049 B1 | 6/2001 |

(Continued)

OTHER PUBLICATIONS

Mikami, JP2007021900A (2007), English Translation.*
All Office Actions, U.S. Appl. No. 16/358,225.
International Search Report and Written Opinion of the International Searching Authority, PCT/US019/022838, dated Jun. 26, 2019, 11 pages.
International Search Report and Written Opinion of the International Searching Authority, PCT/US2016/057476, dated Dec. 20, 2016, 10 pages.
U.S. Appl. No. 62/644,707, filed Mar. 19, 2018, Emily Charlotte Boswell et al.

(Continued)

*Primary Examiner* — Robert A Wax
*Assistant Examiner* — Randeep Singh
(74) *Attorney, Agent, or Firm* — John G. Powell

(57) ABSTRACT

A multi-layered beauty care product is provided. The beauty care product has a layer of a water-soluble film zone with a water-soluble film forming polymer and a cosmetic composition with a skin active agent. The product also has a vapor-deposited coating. The vapor-deposited coating is a poly(p-xylylene) polymer and/or a metal oxide inorganic coating.

25 Claims, 2 Drawing Sheets

(56) References Cited

U.S. PATENT DOCUMENTS

| | | |
|---|---|---|
| 5,559,165 A | 9/1996 | Paul |
| 5,628,737 A | 5/1997 | Dobrin et al. |
| 5,629,014 A | 5/1997 | Kwiatek et al. |
| 5,641,506 A | 6/1997 | Talke et al. |
| 5,713,842 A | 2/1998 | Kay |
| 5,723,138 A | 3/1998 | Bae et al. |
| 5,785,978 A | 7/1998 | Porter et al. |
| 5,820,877 A | 10/1998 | Yamaguchi et al. |
| 5,958,447 A | 9/1999 | Haralambopoulos et al. |
| 5,965,154 A | 10/1999 | Haralambopoulos |
| 5,968,533 A | 10/1999 | Porter et al. |
| 6,162,458 A | 12/2000 | Asada et al. |
| 6,168,028 B1 | 1/2001 | Telesca et al. |
| 6,183,770 B1 | 2/2001 | Muchin et al. |
| 6,200,596 B1 | 3/2001 | Schwartzmiller et al. |
| D440,315 S | 4/2001 | Hassenbein et al. |
| 6,221,369 B1 | 4/2001 | Pool et al. |
| 6,277,401 B1 | 8/2001 | Bello et al. |
| 6,325,565 B1 | 12/2001 | Girardot et al. |
| 6,338,855 B1 | 1/2002 | Albacarys et al. |
| 6,448,303 B1 | 9/2002 | Paul |
| 6,495,158 B1 | 12/2002 | Buseman et al. |
| 6,495,229 B1 | 12/2002 | Carte et al. |
| 6,593,602 B2 | 7/2003 | Liang et al. |
| D484,985 S | 1/2004 | Takizawa et al. |
| 6,673,363 B2 | 1/2004 | Luo et al. |
| 6,676,962 B1 | 1/2004 | Muller |
| 6,730,317 B2 | 5/2004 | Gueret |
| 6,899,840 B2 | 5/2005 | Ueda et al. |
| 6,926,960 B1 | 8/2005 | Hoshino et al. |
| 6,953,602 B2 | 10/2005 | Carte et al. |
| D519,239 S | 4/2006 | Katagiri |
| 7,063,859 B1 | 6/2006 | Kanios et al. |
| 7,256,234 B2 | 8/2007 | Nierle et al. |
| 7,531,185 B2 | 5/2009 | Chen et al. |
| 7,658,942 B2 | 2/2010 | Deckner et al. |
| 7,854,938 B2 | 12/2010 | Ueda et al. |
| 8,066,117 B2 | 11/2011 | Ueda et al. |
| 8,173,233 B2 | 5/2012 | Rogers et al. |
| 8,353,399 B2 | 1/2013 | Ueda et al. |
| 8,512,837 B2 | 8/2013 | Barreneche |
| 8,728,514 B2 | 5/2014 | Choi et al. |
| 9,066,888 B2 | 6/2015 | Kugelmann et al. |
| 9,406,485 B1* | 8/2016 | Cheng ............... H01J 37/32183 |
| 2002/0022052 A1 | 2/2002 | Dransfield |
| 2002/0077266 A1 | 6/2002 | Gabriel et al. |
| 2002/0187181 A1 | 12/2002 | Godbey et al. |
| 2003/0072724 A1 | 4/2003 | Maibach et al. |
| 2003/0082219 A1 | 5/2003 | Warren et al. |
| 2003/0152610 A1 | 8/2003 | Rolf et al. |
| 2003/0167556 A1 | 9/2003 | Kelley |
| 2003/0175328 A1 | 9/2003 | Shefer et al. |
| 2003/0180347 A1 | 9/2003 | Young |
| 2004/0009202 A1 | 1/2004 | Woller |
| 2004/0116018 A1 | 6/2004 | Fenwick et al. |
| 2004/0202706 A1 | 10/2004 | Koo |
| 2005/0013784 A1 | 1/2005 | Trigg et al. |
| 2005/0266059 A1 | 12/2005 | Poss |
| 2006/0104931 A1 | 5/2006 | Fukutome et al. |
| 2006/0121097 A1 | 6/2006 | Lodge et al. |
| 2006/0177487 A1 | 8/2006 | Martz |
| 2006/0198879 A1 | 9/2006 | Fukuta et al. |
| 2007/0020220 A1 | 1/2007 | Osborne |
| 2007/0060855 A1 | 3/2007 | Leung et al. |
| 2007/0254021 A1 | 11/2007 | Scimeca et al. |
| 2007/0259029 A1 | 11/2007 | McEntire et al. |
| 2007/0292491 A1 | 12/2007 | Hansen et al. |
| 2007/0298089 A1 | 12/2007 | Saeki et al. |
| 2008/0014231 A1 | 1/2008 | Okano |
| 2008/0138593 A1 | 6/2008 | Martinez |
| 2008/0260808 A1 | 10/2008 | Pinna et al. |
| 2009/0010998 A1 | 1/2009 | Marchitto et al. |
| 2009/0155326 A1 | 6/2009 | Mack et al. |
| 2009/0234308 A1 | 9/2009 | Jackson et al. |
| 2009/0249558 A1 | 10/2009 | Fileccia et al. |
| 2009/0258062 A1 | 10/2009 | Horstmann |
| 2009/0263600 A1 | 10/2009 | Miyashita et al. |
| 2009/0317578 A1 | 12/2009 | Rogers et al. |
| 2009/0317605 A1 | 12/2009 | Rogers et al. |
| 2010/0239619 A1 | 9/2010 | Hurwitz |
| 2011/0200652 A1 | 8/2011 | Smith et al. |
| 2011/0300198 A1 | 12/2011 | Nussinovitch et al. |
| 2012/0308619 A1 | 12/2012 | Tousley |
| 2013/0042417 A1 | 2/2013 | Smith et al. |
| 2013/0178407 A1 | 7/2013 | Fileccia et al. |
| 2014/0079938 A1 | 3/2014 | Perick et al. |
| 2014/0083878 A1 | 3/2014 | Tang et al. |
| 2014/0276478 A1 | 9/2014 | Liao et al. |
| 2014/0376835 A1 | 12/2014 | Rogers et al. |
| 2014/0377512 A1 | 12/2014 | Rogers et al. |
| 2015/0209243 A1 | 7/2015 | Shiroya et al. |
| 2015/0307264 A1 | 10/2015 | Boswell et al. |
| 2015/0320606 A1 | 11/2015 | Kawahara |
| 2016/0107004 A1 | 4/2016 | Wilder et al. |
| 2017/0042311 A1 | 2/2017 | Wilder et al. |
| 2017/0112724 A1 | 4/2017 | Boswell et al. |
| 2017/0112725 A1 | 4/2017 | Boswell et al. |
| 2017/0112726 A1 | 4/2017 | Boswell et al. |
| 2017/0112727 A1 | 4/2017 | Boswell et al. |
| 2018/0098921 A1 | 4/2018 | Boswell et al. |
| 2018/0193229 A1 | 7/2018 | Boswell et al. |
| 2018/0193230 A1 | 7/2018 | Boswell et al. |
| 2018/0200158 A1 | 7/2018 | Boswell et al. |
| 2018/0360698 A1 | 12/2018 | Boswell |
| 2019/0282459 A1 | 9/2019 | Boswell |

FOREIGN PATENT DOCUMENTS

| | | | |
|---|---|---|---|
| EP | 2316436 A1 | | 5/2011 |
| EP | 2316438 A1 | | 5/2011 |
| EP | 2559425 A1 | | 2/2013 |
| GB | 2221620 B | | 9/1991 |
| JP | S5052044 U | | 5/1975 |
| JP | 2002249422 A | | 9/2002 |
| JP | 2004051516 A | | 2/2004 |
| JP | 2006021789 | | 1/2006 |
| JP | 2007021900 A | * | 2/2007 |
| JP | 2011178693 | | 2/2010 |
| KR | 20080014461 A | | 2/2008 |
| KR | 100871282 B1 | | 11/2008 |
| WO | WO9216202 A1 | | 10/1992 |
| WO | WO9528136 A1 | | 10/1995 |
| WO | WO1996014822 | | 5/1996 |
| WO | WO97032567 A1 | | 9/1997 |
| WO | WO9748387 A1 | | 12/1997 |
| WO | WO9926572 A1 | | 6/1999 |
| WO | WO2000030694 | | 6/2000 |
| WO | WO0075220 A1 | | 12/2000 |
| WO | WO2001001816 | | 1/2001 |
| WO | WO2001001951 | | 1/2001 |
| WO | WO2001001952 | | 1/2001 |
| WO | WO2001078678 | | 10/2001 |
| WO | WO03063817 A1 | | 8/2003 |
| WO | WO03084579 A1 | | 10/2003 |
| WO | WO2004077990 A1 | | 9/2004 |
| WO | WO2004078122 A2 | | 9/2004 |
| WO | WO2006062740 A3 | | 8/2006 |
| WO | WO2008071310 A1 | | 6/2008 |
| WO | WO2009055048 A1 | | 4/2009 |
| WO | WO2010057189 A1 | | 5/2010 |
| WO | WO2014079459 A1 | | 5/2014 |

OTHER PUBLICATIONS

U.S. Appl. No. 15/843,866, filed Dec. 15, 2017, Emily Charlotte Boswell et al.
All Office Actions, U.S. Appl. No. 14/919,048.
All Office Actions, U.S. Appl. No. 14/918,989.
All Office Actions, U.S. Appl. No. 15/296,630, case No. 14080MQL.
All Office Actions, U.S. Appl. No. 15/296,713, case No. 14081M.
All Office Actions, U.S. Appl. No. 15/296,736, case No. 14082MQL.
All Office Actions, U.S. Appl. No. 15/839,287, case No. 14082MCQL.
All Office Actions, U.S. Appl. No. 15/843,812, case No. 14650M.

(56) References Cited

OTHER PUBLICATIONS

All Office Actions, U.S. Appl. No. 15/843,866, case No. 14651M.
All Office Actions, U.S. Appl. No. 15/865,384, case No. 14502M.
All Office Actions, U.S. Appl. No. 15/865,402, case No. 14502M2.
All Office Actions, U.S. Appl. No. 15/296,768, case No. 14082M2QL.
How to Make Water-in-Oil (W/O) Emulsions, Making Cosmetics Inc., http://www.makingcosmetics.com/articles/27-how-to-make-water-in-oil-emulsions.pdf, retrieved online on Mar. 20, 2014.
International Search Report and Written Opinion of the International Searching Authority, PCT/US2015/056667, dated Dec. 21, 2015, 13 pages.
International Search Report and Written Opinion of the International Searching Authority, PCT/US2015/056670, dated Dec. 21, 2015, 16 pages.
International Search Report and Written Opinion of the International Searching Authority, PCT/US2016/057470, dated Dec. 20, 2016, 10 pages.
International Search Report and Written Opinion of the International Searching Authority, PCT/US2016/057472, dated Dec. 23, 2016, 12 pages.
International Search Report and Written Opinion of the International Searching Authority, PCT/US2018/012869, dated Apr. 30, 2018, 12 pages.
International Search Report and Written Opinion of the International Searching Authority, PCT/US2018/012870, dated Apr. 30, 2018, 13 pages.
International Search Report and Written Opinion of the International Searching Authority, PCT/US2018/012871, dated May 28, 2018, 10 pages.
International Search Report and Written Opinion of the International Searching Authority, PCT/US2018/012873, dated May 28, 2018, 10 pages.
International Search Report and Written Opinion of the International Searching Authority, PCT/US2018/038896, dated Oct. 5, 2018, 10 pages.
Ovington, Liza G., Advances in Wound Dressings, Clinics in Dermatology, 2007, vol. 25, pp. 33-38.
PCT International Search Report, dated Dec. 20, 2016, 10 pages.
Schut, J., Foamed Films Find New Niches, Plastics Technology, Jan. 2002 Issue, 5 pages.
www.gnpd.com Record ID: 1119887, Day Out First Aid Kit, Savlon, Jun. 2009.

* cited by examiner

FILMS INCLUDING A WATER-SOLUBLE LAYER AND A VAPOR-DEPOSITED COATING

TECHNICAL FIELD

The present invention relates to products, comprising a water-soluble layer having a skin active agent and a vapor deposited coating, for improving skin appearance.

BACKGROUND OF THE INVENTION

The benefits of using a patch or mask device comprising skin agents to cosmetically treat the skin, have been recognized in the art. A variety of cosmetic patches or devices are commercially marketed or described as being useful for the delivery of skin actives. Patches have also been described in the literature and marketed in the medical field as a useful means for the transdermal administration of drugs.

However, many patches or devices suffer drawbacks which include ineffective release of the active ingredients to the skin. Other patches are dry, rough, and inflexible and thus are tight and uncomfortable to wear. Many existing cosmetic patches typically comprise flat two-dimensional substrates. These substrates remain in this inflexible configuration during wear and do not conform well to three dimensional surfaces of the skin. Existing patches are not able to conform as the facial skin flexes and changes during movement and changing facial expressions. Thus, in this dynamic environment, these patches often do not conform well to the contours of the skin surface to which they are applied. Gaps between the skin surface and the patch may form or the patch may simply be uncomfortable to wear especially for long periods of time. Thus, many patches have undesirable in-use characteristics.

Thus, an improved multilayered beauty care product is provided. The product comprises a soluble film zone containing the active agent and a water-soluble film forming polymer. In an aspect as the soluble film forming polymer dissolves, the active is released. The product also comprises a thin, vapor-deposited coating. Despite its minimal thickness the product provides good barrier and occlusive properties. This avoids having to substantially increase the thickness of the product and/or use a thick backing layer that may increase the product's stiffness and decrease comfort in use by the consumer. Thus, the product has improved comfort and conformability around the curved surfaces of the skin.

SUMMARY OF THE INVENTION

In one aspect, a multi-layered beauty care product for applying a skin active agent to the skin, is provided comprising:
 a layer of a water-soluble film zone comprising:
 a top surface and a bottom surface;
 a water-soluble film forming polymer;
 a cosmetic composition comprising an effective amount of a skin active agent; and
 a vapor-deposited coating, wherein the vapor-deposited coating is selected from the group consisting of a poly(p-xylylene) polymer, a metal oxide inorganic coating, and combinations thereof.

BRIEF DESCRIPTION OF THE DRAWINGS

While the specification concludes with claims that particularly point out and distinctly claim the invention, it is believed that the present invention will be better understood from the following description of aspects, taken in conjunction with the accompanying drawings in which:

DETAILED DESCRIPTION OF THE INVENTION

Figure 1:
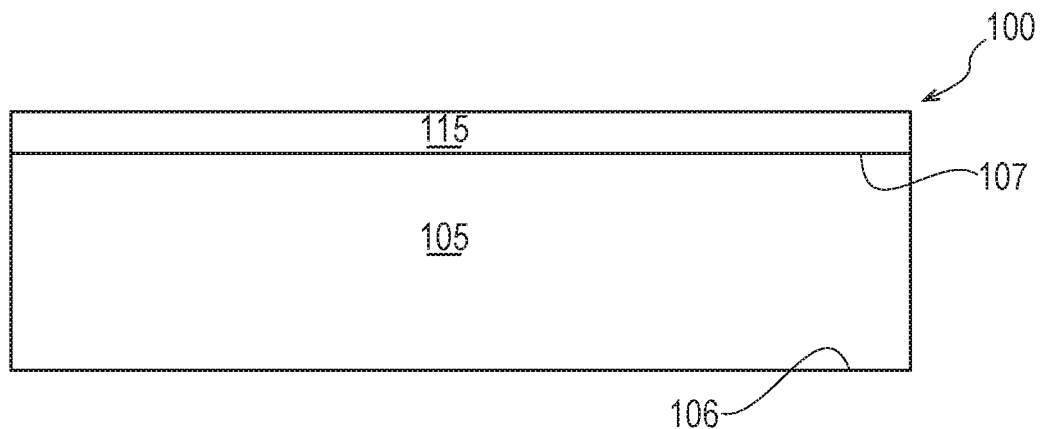
FIG. 1 depicts a cross-sectional view of a product.

While the specification concludes with the claims particularly pointing out and distinctly claiming the invention, it is believed that the present invention will be better understood from the following description.

All percentages and ratios used herein are by weight of the total composition. All numeric ranges are inclusive of narrower ranges; delineated upper and lower range limits are interchangeable to create further ranges not explicitly delineated. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity.

As used herein, "molecular weight" or "Molecular weight" refers to the weight average molecular weight unless otherwise stated. Molecular weight is measured using industry standard method, gel permeation chromatography ("GPC").

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods.

The term "apply" or "application" as used in reference to a composition, means to apply or spread the compositions onto a substrate such as the human skin surface or epidermis.

The term "dermatologically acceptable," as used herein, means that the compositions or components thereof so described are suitable for use in contact with mammalian keratinous tissue without undue toxicity, incompatibility, instability, allergic response, and the like.

The term "facial skin surface" as used herein refers to one or more of forehead, periorbital, cheek, perioral, chin, and nose skin surfaces. While facial skin surfaces are of concern and are exemplified herein, other skin surfaces may be treated with the compositions and methods of the present invention, for example, surfaces typically not covered by clothing such as facial skin surfaces, hand and arm skin surfaces, foot and leg skin surfaces, and neck and chest skin surfaces (e.g., decolletage).

As used herein "healthy skin" means that the physical barrier function of the epidermis and the dermis is maintained intact for example, the stratum corneum of skin is intact, and is not physically disrupted, removed, subject to reduction, wounded, altered or ablated using mechanical, optical, or thermal means.

The term "keratinous tissue," as used herein, refers to keratin-containing layers disposed as the outermost protective covering of mammals (e.g., humans, dogs, cats, etc.) which includes, but is not limited to, skin, mucosa, lips, hair, toenails, fingernails, cuticles, hooves, etc.

The terms "topical application", "topically", and "topical", as used herein, mean to apply (e.g., spread, spray) the compositions of the present invention onto the surface of the keratinous tissue.

As used herein, "effective amount" means an amount of a compound or composition sufficient to significantly induce a positive keratinous tissue benefit, including independently or in combination with other benefits disclosed herein. This means that the content and/or concentration of agent in the formulation is sufficient that when the formulation is applied with normal frequency and in a normal amount, the formulation can result in the treatment of one or more undesired keratinous tissue conditions (e.g., skin wrinkles). For instance, the amount can be an amount sufficient to inhibit or enhance some biochemical function occurring within the keratinous tissue. This amount of the skin care agent may vary depending upon the type of product, the type of keratinous tissue condition to be addressed, and the like.

The term "safe and effective amount" as used herein means an amount of a compound or composition sufficient to significantly induce a positive benefit, preferably a positive keratinous tissue appearance, including independently or in combinations with the benefits disclosed herein, but low enough to avoid serious side effects, i.e., to provide a reasonable benefit to risk ratio, within the scope of sound judgment of the skilled artisan.

As used herein, the term "water impermeable" includes materials or objects through which water in its liquid state does not pass.

The term "substantially free of" refers to an amount of a material that is less than 2%, 1%, 0.5%, 0.25%, 0.1%, 0.05%, 0.01%, or 0.001% by weight, of product, the barrier patch, the water-soluble film zone, the water-soluble film forming polymer, or the backing layer of the barrier patch. "Free of" refers to no detectable amount of the stated ingredient or thing.

As used herein, the term "nonwoven" means a porous, fibrous material made from continuous (long) filaments (fibers) and/or discontinuous (short) filaments (fibers) by processes such as, for example, spunbonding, meltblowing, carding, and the like. Nonwoven webs do not have a woven or knitted filament pattern.

As used herein, the term "vapor-deposited coating" means a coating of a material that is applied to a surface utilizing vaporization of the material.

Water Soluble Layer and a Vapor-Deposited Coating

Products including a layer of water-soluble film zone and a vapor-deposited coating (organic, inorganic, and combinations) are disclosed. As an example, a cross-sectional view of an exemplary product is depicted in FIG. 1. As illustrated in FIG. 1, a film or product 100 can include a water-soluble layer 105 (also referred to herein as a layer of a water-soluble film zone) formed of a water-soluble polymeric material and having a top surface 106 and a bottom surface 107. The product also has a vapor-deposited coating (or vapor deposited organic coating) 115 joined to the bottom surface 107 of the water-soluble layer 105.

As can be appreciated, the products described herein can have many variations. For example, a film or product can include a vapor-deposited coating on only one surface of the water-soluble layer as depicted in FIG. 1 or can have a vapor-deposited coating on both surfaces, the top surface 106 and the bottom surface 107, of the water-soluble layer in certain aspects (not depicted) provided that at least some of the water-soluble layer is at least partially uncoated on the skin facing surface of the product.

In certain aspects, a film can additionally include one, or more, intermediate layers between the water-soluble layer and the vapor-deposited coating. For example, the film or product 200, depicted in FIG. 2, includes a water-soluble layer 205 (also referred to herein as a layer of a water-soluble film zone), a vapor-deposited inorganic coating 210 joined to one surface of the water-soluble layer 205, and a vapor-deposited organic coating 215 joined to the vapor-deposited inorganic coating 210. Additional intermediate layers, or additional coating layers, such as indicia layers, can further be included. As can further be appreciated, the order of the layers can also vary. For example, a vapor-deposited organic coating can be joined to one surface of the water-soluble layer and a vapor-deposited inorganic coating can be joined to the vapor-deposited organic coating.

Figure 2:
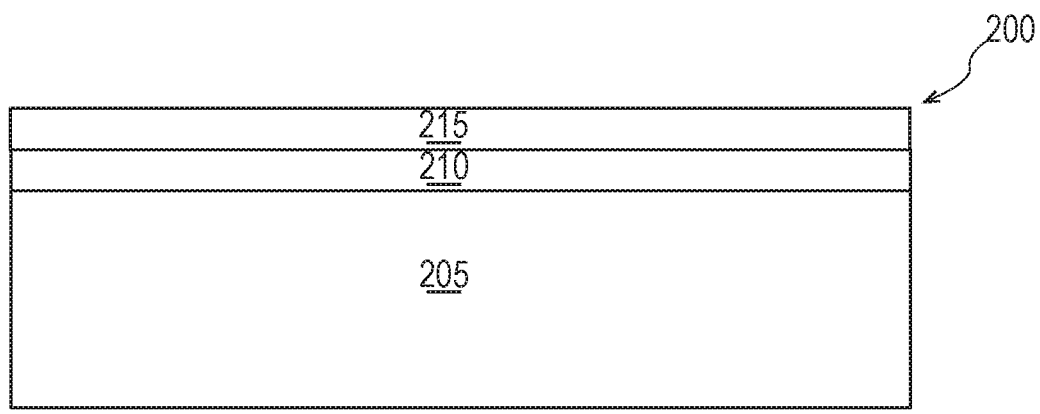
FIG. 2 depicts a cross-sectional view of an alternate product.

In the execution illustrated by FIGS. 1 and 2, some water soluble layers are sticky enough (when particular polymer combinations are selected, especially those containing PVP), that when wetted they will adhere directly to skin. Such executions may not require an additional adhesive as long as the consumer is willing to wet their skin prior to applying the product. In this execution, the coated water soluble film layer simply needs to be die cut to the required shape.

The product may have multiple vapor-deposited coatings. The product may also include more than one water-soluble layer. For example, a film as described herein can include two water-soluble layers, three water-soluble layers, five water-soluble layers, or more water-soluble layers.

Figure 3:
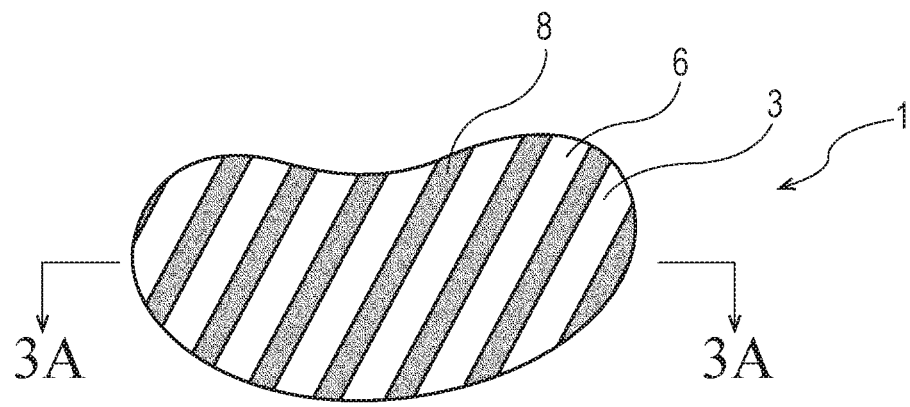
FIG. 3 depicts a top view of a product.
Figure 3A:
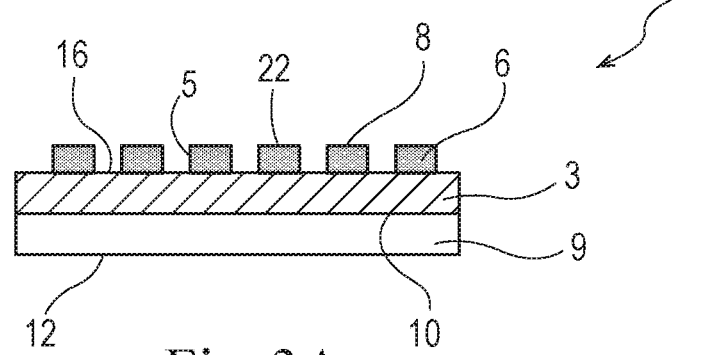
FIG. 3A depicts a cross-sectional view of the product of FIG. 3.
Figure 4:
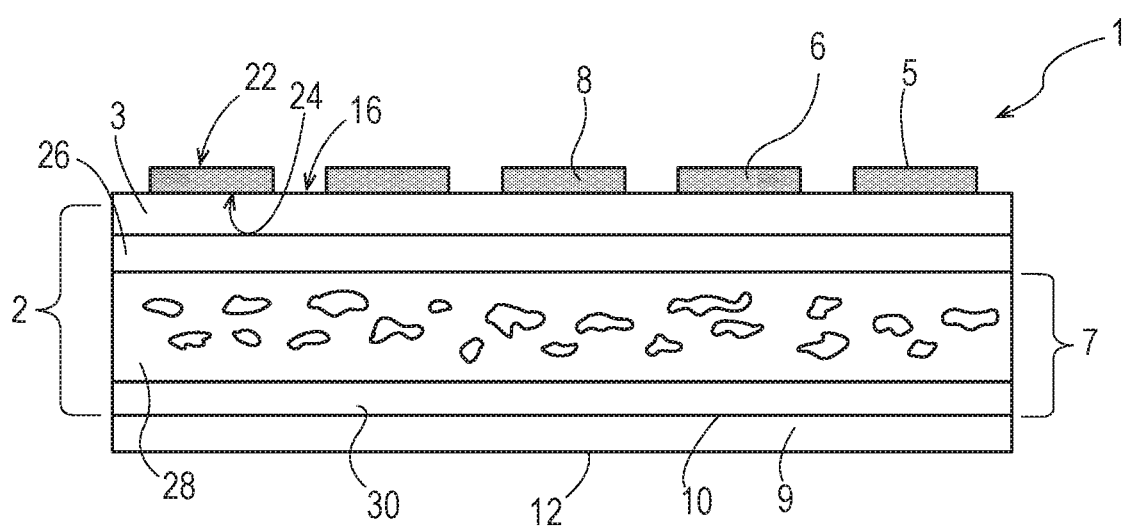
FIG. 4 depicts a cross-sectional view of an alternative product.

Exemplary aspects of the product 1 are shown in FIGS. 3, 3A, and 4. FIGS. 3 and 3A show product 1 comprising a water-soluble film zone 6, a pressure sensitive adhesive 3 and a vapor deposited organic coating 9. FIG. 3A is the cross section of FIG. 3 taken along 3A-3A. FIGS. 3 and 3A show a plurality of soluble film zones 6 to create a series of parallel stripes offset to the longitudinal axis of the product 1. The product 1 thus has alternative rows of stripes of the soluble film zones 6 applied to the upper surface 16 of the pressure sensitive adhesive 3.

The product 1 further comprises a soluble film zone 6 having an effective amount of a skin active agent 8. The vapor deposited organic coating 9 further comprises a first surface 10 and a second surface 12. The pressure sensitive adhesive 3 is in contact with at least part of the first surface 10 of the vapor deposited organic coating 9. The product 1 may further comprise a cosmetic composition comprising an effective amount of a skin active agent 8. In one aspect, the pressure sensitive adhesive 3 also comprises the cosmetic composition. In other aspects, the cosmetic composition and skin active agent 8 are distributed to some extent and/or are homogeneously distributed throughout the soluble film zone 6. The product 1 has a skin facing surface 5. The skin facing surface 5 of the product 1 may comprise the upper surface 16 of the pressure sensitive adhesive, the top surface 22 of the water-soluble film zone and/or the first surface 10 of the vapor deposited organic coating.

In an aspect FIGS. and, 3A, the product 1 is crescent shaped. However, this shape is not intended to limit the invention.

FIG. 4 shows an alternative cross section of the product 1. FIG. 4 shows the product 1 comprising a barrier patch 2 having a pressure sensitive adhesive 3 and a backing layer 7. The product 1 further comprises a soluble film zone 6 having an effective amount of a skin active agent 8. The vapor deposited organic coating 9 further comprises a first surface 10 and a second surface 12. The backing layer 7 comprises 3 layers: a non-foamed first layer 26, a foamed second layer 28 and a non-foamed third layer 30. The pressure sensitive adhesive 3 comprises an upper surface 16 and a lower surface 18. The water-soluble film zone 6 also comprises a top surface 22 and a bottom surface 24. As shown the bottom surface 24 of the plurality of soluble film zones 6 are in contact with the upper surface 16 of the pressure sensitive adhesive 3. As shown in FIGS. 3, 3A and 4 the soluble film zones 6 and the pressure sensitive adhesive 3 are substantially separate and the pressure sensitive adhesive zone 3 is continuous. The first surface 10 of the vapor deposited coating is in contact with the backing layer 7.

In one aspect, the skin active agent 8 is distributed to some extent and/or homogeneously distributed throughout each of the plurality of the soluble film zones 6.

Water-Soluble Film Zone

The water-soluble film zone comprises a water-soluble film forming polymer and a cosmetic composition comprising an effective amount of a skin active agent. The water-soluble film forming polymer forms a water-soluble film. As used herein "water-soluble film" means a film that dissolves according to the dissolution method herein.

In an aspect, the water-soluble film zone comprises from about 30% to about 99% or from about 40% to about 90%, more preferably from about 50% to about 75% of a water-soluble film forming polymer.

As used herein a "low water environment" of the skin, means the humidity or moisture provided, under occlusion, from the inner skin layer(s) of healthy skin to the surface of the skin via the pores in the skin. This may comprise components of sweat, sebum or oil. For example, a low water environment includes the humidity build up on the skin when the product herein is applied to the skin for about 1 to 8 hours or longer, the product comprising a low breathability (e.g. low WVTR, the proper thickness, etc.), as provided herein.

The water-soluble film zone or product is thus capable of increasing in weight as the buildup of water/humidity occurs under the product when applied to the skin. As this transformation occurs, the skin active agent may be released from the product to the skin of the user and be absorbed into the skin to have the intended effect.

Once the soluble film or product is exposed to a low water environment and/or is occluded on the skin as described herein, it has a weight change that is higher than the initial weight.

The water-soluble film zone or product is also capable of decreasing in modulus as the buildup of water/humidity occurs under the product when applied to the skin. Thus, the product or water-soluble film zone provides a "dynamic" modulus where the modulus decreases during wear to improve the comfort of the product. As this transformation occurs, the skin active agent may be released from the product to the skin to have the intended effect.

Without being bound by theory, the soluble film zone or soluble film dissolves, disintegrates, and/or loses its physical integrity when exposed to low water environments. As the water-soluble film zone or water-soluble film softens and/or dissolves, the active is released. The soluble film zone or water-soluble film, prior to exposure to a low water environment, is a dry film comprising a water-soluble polymer. In this dry state, it has a first modulus and the water-soluble film zone, water-soluble film or product also comprises a weight, e.g. an initial weight. In an aspect, once the soluble film or product is exposed to a low water environment and/or is applied to the skin so that the skin is occluded, as described herein, it has a second modulus that is lower than the first modulus and also has a second weight that is higher than the initial weight.

In an aspect, the water-soluble film zone or water-soluble film has a first modulus that is higher than the modulus of the backing layer or barrier patch. For example, after wearing on the skin at 37° C., at 90% RH, the water-soluble film zone or water-soluble film has a second modulus that is lower than the modulus of the backing layer or barrier patch. In an aspect, this provides a product that is more comfortable to wear and more easily conforms around the curved surfaces of the skin, especially upon movement of the skin surfaces.

In an aspect, the soluble film zone comprises a skin active agent. In an aspect, the skin active agent is only minimally released, if at all, from the soluble film zone in the dry form prior to use and/or prior to exposure to the low water environment and/or in the absence of moisture or water. When a low level of water, contacts the soluble film zone, softening, dissolution or breakdown, begins to occur, thereby enabling the skin active to migrate out of the soluble film zone and/or penetrate to the skin surface or into the skin. In an aspect in the presence of water, skin active agents present in the soluble film zones are believed to be more readily available to the skin due to the faster rates of diffusion through the soluble film zone.

In an aspect, prior to use by the consumer, the water-soluble film zone is substantially free of water or may comprise less than about 15%, 12%, or 10%, water, or comprise about 0.001% to about 15% water, or about 0.05% to about 10%, water, by weight of the soluble film zone.

Preferred water-soluble materials for the soluble film zone are polymeric materials, preferably polymers which may be formed into a film or sheet. The water-soluble film zone can, for example, be obtained by casting, blow-molding, extrusion or blown extrusion of the polymeric material, as known in the art.

Preferred water-soluble materials for the soluble film zone may be selected from polyethylene oxide polymers, polyvinyl alcohols, polyvinyl pyrrolidone, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum, polyacrylates and water-soluble acrylate copolymers, polymethacrylates, methylcellulose, carboxymethylcellulose, hydroxyethyl cellulose, hydroxypropyl methylcellulose, dextrin, maltodextrin, salts thereof, and combinations thereof.

Water-soluble materials for the soluble film zone may be selected from polyethylene glycol, pullulan, carbohydrate polymers such as natural polysaccharide or derivates including pectin and derivatives, sodium alginate, methyl methacrylate copolymer, carboxyvinyl polymer, amylase, pectin, chitin, chitosan, levan, elsinan, collagen, gelatine, zein, gluten, soy protein isolate, whey protein isolate, casein, gums (such as guar, gum Arabic, tragacanth gum, xanthan gum, gellan sodium salt, gum ghatti, okra gum, karaya gum, locust bean gum, tara gum, quince seed gum, fenugreek seed gum, scleroglucan, psyllium seed gum, tamarind gum, oat gum, quince seed gum, rhizobium gum, biosynthetic gums, Khaya grandifolia gum, pectin, arabian, Konjac mannan, alactomannan, funoran, acetan, welan, rhamsan, furcelleran, succinoglycan, scleroglycan, and dextran, flaxseed gum), propyleneglycol, alginate, starches (such as amylose, amylopectin, modified starches, hydroxyethyl starch, carboxymethyl starch, high amylose starch, hydrooxypropylated high amylose starch, biosynthetic processed starch, starches such as rice, corn, potato, and wheat), dextrans, dextrins and maltodextrins, konjac, acemannan from aloe, carrageenans, scleraglucan, succinoglucan, larch arabinogalactan, chondroitin sulfates, hyaluronic acid, curdlan, deacetylatedkonjac, water-soluble non-gelling polypeptide or protein (such as gelatins, albumins, milk proteins, soy protein, and whey proteins), hydrocolloids (such as synthetic hydrocolloids exemplified by polyethylene-imine, hydroxyethyl cellulose, sodium carboxymethyl cellulose, carboxymethyl cellulose, hydroxypropyl cellulose, hydroxypropyl methyl cellulose, methyl cellulose, ethyl cellulose, polyacrylic acids, low molecular weight polyacrylamides and their sodium salts (carbomers), polyvinylpyrrollidone, polyethylene glycols, polyethylene oxides, polyvinyl alcohols, pluronics, tetronics, and other block co-polymers, carboxyvinyl polymers, and colloidal silicon dioxide, soluble polyesters, natural seaweeds, natural seed, natural plant exudates, natural fruit extracts, glycyrrhizic acid, polyacrylic acid, vinyl polymers, cationic polymers, acrylic polymers (such as sodium polyacrylate, polyethyleacrylate and polyacrylamide), and combinations.

In an aspect, the water-soluble film zone comprises a polymer selected from the group consisting of polyethylene oxide polymer, polyvinyl alcohols, polyvinyl alcohol copolymers, starch, methylcellulose, carboxymethylcellulose sodium, hydroxyethyl cellulose, hydroxypropyl methylcellulose and combinations thereof.

Preferred polymers, copolymers or derivatives thereof suitable for use as water-soluble film for the soluble film zone are selected from polyethylene oxides, and combinations thereof.

Preferred polymers, copolymers or derivatives thereof suitable for use as water-soluble film for the soluble film zone are selected from methylcelluloses, and combinations thereof.

Preferred water-soluble film forming polymers are made from polyethylene oxides such as polyethylene oxide films or polyethylene glycol, and include Polyox, sold by the Dow Chemical Company. Polyethylene oxides include Polyox WSR N-10 (having a molecular weight of 10.000). WSR N-80 (with a molecular weight of about 200.000). WSR N 750 (with a molecular weight of about 300,000) of corresponding solubility characteristics. In an aspect, the water-soluble film comprises a polyethylene oxide having a molecular weight from about 500 to about 10,000,000 or from about 10,000 to about 1,000,000 or from about 100,000 to about 300,000 or from about 150,000 to about 250,000.

Another preferred water-soluble film forming polymer is Methocel E5LV, a water-soluble cellulose ether of low viscosity available from Dow/Coloron LTD.

The polyethylene oxide polymers or cellulose ether may be combined with additional polymers, for example, polymers, copolymers or derivatives thereof which may be other water-soluble film forming polymers. The additional polymers may be selected from polyvinyl alcohols, polyvinyl pyrrolidone, polyalkylene oxides, acrylamide, acrylic acid, cellulose, cellulose ethers, cellulose esters, cellulose amides, polyvinyl acetates, polycarboxylic acids and salts, polyaminoacids or peptides, polyamides, polyacrylamide, copolymers of maleic/acrylic acids, polysaccharides including starch and gelatin, natural gums such as xanthum and carragum, polyacrylates and water-soluble acrylate copolymers, polymethacrylates, methylcellulose, carboxymethylcellulose, hydroxyethyl cellulose, hydroxypropyl methylcellulose, dextrin, maltodextrin, salts thereof, and combinations thereof. In an aspect, the water-soluble film zone comprises polyethylene oxide polymer and an additional polymer selected from the group consisting of polyvinyl alcohols, polyvinyl alcohol copolymers, starch, methylcellulose, carboxymethylcellulose sodium, hydroxyethyl cellulose, hydroxypropyl methylcellulose and combinations.

Also suitable are mixtures of polyethylene oxide polymers having different molecular weights. The additional polymers may have molecular weights, preferably from about 1,000 to 1,000,000, more preferably from about 50,000 to 300,000 yet more preferably from about 20,000 to 150,000.

In another aspect, the cosmetic composition may comprise a water in oil or an oil in water emulsion to be combined with a water-soluble film forming polymer. As an example, an oil in water emulsion composition such as Olay skin care product may be combined with methylcellulose or hydroxypropyl methylcellulose such as Methocel E5LV (available from Dow Chemical) and used as the water-soluble film zone. The water-soluble film forming polymer, such as Methocel, may be used in excess of the composition comprising the oil in water emulsion with skin active agent. In an aspect, thus, the water-soluble film zone may comprise:

a.) from about 40% to about 70% by weight of the soluble film zone, of a water-soluble film forming polymer;
b.) from about 30% to about 60% by weight of the soluble film zone, of a cosmetic composition comprising a water in oil or an oil in water emulsion and an effective amount of a skin active agent; and
c.) optionally a safe and effective amount of a plasticizer.

In an aspect, the ratio of b) to a) in the soluble film zone, is from about 30:70 to about 70:30 or from about 40:60 to about 60:40 or about 45:55 to about 55:45 in either the wet or dry state.

Plasticizer

The water-soluble film zone herein can also comprise one or more plasticizers. For example, it can be beneficial to add plasticizers at a level of from about 2% to about 80% or about 2% to about 60%, by weight of the soluble film zone or the water-soluble film forming polymer, or from about 10% to about 50% or from about 20% to about 45% by weight. The plasticizers may be (other than water), for example, glycerol, ethylene glycol, diethylene glycol, hexylene glycol, triethylene glycol, propylene glycol, polyethylene glycol, polypropyl glycol, alkyl citrate, sorbitol, pentaerythritol, glucamine, N-methylglucamine, sodiumcumenesulfonate and mixtures thereof. In one aspect, the plasticizer is glycerol. Other plasticizers may include vegetable oil, polysorbitols, polyethylene oxide, dimethicone, mineral oil, paraffin, C1-C3 alcohols, dimethyl sulfoxide, N, N-dimethylacetamide, sucrose, corn syrup, fructose, dioctyl-sodium-sulfo-succinate, triethyl citrate, tributyl citrate, 1,2-propylenglycol, mono, di- or triacetates of glycerol, natural gums, citrates, and mixtures thereof.

Optional Ingredients for Soluble Film Zone

The water-soluble film zone or water-soluble film forming polymer herein can also comprise one or more optional ingredients. Optional ingredients include bulking agents, fillers, diluents, surfactants, stabilizing agents, emulsifiers, thickeners, preservatives, binders, colorants, pigments, solubilizing agents, wetting agents, water-soluble inert fillers, buffering agents, permeation enhancers, and combinations. Thickeners may include gum arabic, carrageenan, karaya gum, gum tragacanth, carob gum, quince seed or *Cydonia oblonga*, casein, dextrin, gelatin, sodium pectate, sodium alginate, methyl cellulose, ethyl cellulose, CMC, hydroxy ethyl cellulose, hydroxypropyl cellulose, polyvinyl alcohol, PVM, PVP, sodium polyacrylate, carboxy vinyl polymer, locust bean gum, guar gum, tamarind gum, cellulose dialkyl dimethylammonium sulfate, xanthan gum, aluminum magnesium silicate, bentonite, hectorite, AlMg silicate or beagum, laponite, and silicic acid anhydride.

Surfactants may include mono and diglycerides of fatty acids and polyoxyethylene sorbitol esters, such as, Atmos 300 and Polysorbate 80, pluronic acid, and sodium lauryl sulfate.

Stabilizing agents may include xanthan gum, locust bean gum and carrageenan, guar gum, sugars, polyols, amino acids or methylamines. Emulsifying agents may include triethanolamine stearate, quaternary ammonium compounds, acacia, gelatin, lecithin, bentonite, veegum, sodium benzoate.

Permeation enhancers may include azone, alcohol, dimethyl-sulfoxide, monovalent, saturated and unsaturated aliphatic and cycloaliphatic alcohols having 6 to 12 carbon atoms such as cyclohexanol, lauryl alcohol, and the like; aliphatic and cycloaliphatic hydrocarbons such as mineral oil; cycloaliphatic and aromatic aldehydes and ketones such as cyclohexanone; N,N-di(lower alkyl)acetamides such as N,N-diethyl acetamide and N,N dimethyl acetamide, N,N-dimethyl acetamide, N-(2-hydroxyethyl)acetamide and the like; aliphatic and cycloaliphatic esters such as isopropyl myristate and lauricidin; N,N-di(lower alkyl) sulfoxides such as decylmethyl sulfoxide; essential oils, nitrated aliphatics, aliphatic and cycloaliphatic hydrocarbons such as N-methyl-2-pyrrolidone and azone; salicylates, polyalkylene glycol silicates; aliphatic acids such as oleic acid and lauric acid, terpines such as cineole, siloxanes such as hexamethyl siloxane; and mixtures.

Vapor-Deposited Organic Coating

Application of a vapor-deposited organic coating can improve the properties and performance of a film in numerous ways. For example, films including a vapor-deposited organic coating can exhibit desirable chemical and physical properties including improved barrier properties, controlled dissolution times, and decreased tackiness. These improved properties can make such films useful for the formation of products typically formed from uncoated water-soluble films as a component. As can be appreciated however, the films described herein can also be useful for other articles and applications due to the excellent mechanical and chemical properties exhibited by the films. In certain aspects, the vapor-deposited organic coatings described herein can be formed of a poly(p-xylylene) polymer.

As can be appreciated, poly(p-xylylene) polymers are generally water insoluble polymers. It has unexpectedly been found, however, that application of vapor-deposited poly(p-xylylene) polymers to a surface of a water-soluble layer can form advantageous films. For example, in certain aspects, the films can retain certain water-solubility benefits while enhancing properties such as the film's barrier strength. In certain such aspects, immersion of the product in water can cause the vapor-deposited organic coating to disintegrate into small and free flowing particles, or other remnants. Such remnants can be disposed, for example, in sewage streams without causing undesirable accumulation or other impermissible detriments. In certain aspects, the remnants can be undetectable. In other aspects, the films/products can be at least partially water insoluble but can exhibit beneficial properties such as desirable barrier properties. In certain aspects, the coatings are not water-soluble.

Generally, poly(p-xylylene) polymers can be vapor-deposited and joined to a water-soluble layer or backing layer through a suitable chemical vapor deposition process. For example, the poly(p-xylylene) polymers can be vapor-deposited using a thermal-based chemical vapor deposition process or a plasma-assisted chemical vapor deposition process in certain aspects.

In certain aspects, a thermal-based chemical vapor deposition can be used. For example, certain vapor-deposited organic coatings described herein can be formed from a chemical vapor deposition process which includes the steps of vaporizing a poly(p-xylylene) polymer precursor, pyrolyzing the poly(p-xylylene) polymer precursor to form a poly(p-xylylene) monomer, and cooling the poly(p-xylylene) monomer to cause condensation and polymerization of the monomer on at least one surface of a layer of water-soluble film zone.

As can be appreciated, plasma-assisted chemical vapor deposition processes can alternatively be used. Plasma-assisted chemical vapor deposition processes can be particularly advantageous because such processes can allow for formation of a poly(p-xylylene) polymer coating while minimizing melting, or other damage, to the water-soluble layer.

In certain aspects, the poly(p-xylylene) polymer precursor can be dichloro-di(p-xylylene) which forms poly(chloro-p-xylylene) polymer. In certain such aspects, there are several stages to forming the poly(chloro-p-xylylene) coating, inside a sealed system that has multiple tubes and chambers that allow gas to flow from the vaporizer section, through the pyrolysis zone, into the deposition chamber, past the probe cold trap and then through the vacuum pump, which exhausts to atmosphere. First the solid dichloro-di(p-xylylene) dimer is vaporized/sublimed at a temperature of 150° C. under a pressure of 13.3 Pa (0.1 torr) inside the vaporizer tube. The dimer gas then flows (under the pumping action of the vacuum pump) through the pyrolysis zone (a high temperature tube furnace) and is pyrolyzed at 690° C. and 66.7 Pa (0.5 torr) which causes the dimer gas to be cleaved to form chloro-p-xylylene gas. This gas then flows into the chemical vapor deposition chamber which contains the film substrate. This chamber is held at a temperature of about 25° C. and a pressure of 6.7 Pa (0.05 torr), though the pressure does rise slightly by about 15-30 milliTorr as the dimer gas flows into it, until the vaporization step is complete. Within this deposition chamber, the chloro-p-xylylene gas condenses and polymerizes to form a coating of poly(chloro-p-xylylene) on the surface of the inorganic coating. Once deposition to the desired thickness is complete, the chamber can be brought up to atmospheric pressure and the film substrate can be removed. In another aspect the inorganic coating may be eliminated and the organic coating may be coated on the surface of the water soluble layer. If this is done, the film, optionally, can be first be ablated to maximize adhesion to the film substrate. Ablation can be achieved using a helium-oxygen plasma or an argon-oxygen plasma at a flow rate of 30.0 L/min at 100 W to about 150 W of power.

As can be appreciated, alternative poly(p-xylylene) polymer precursors can similarly be utilized to form a variety of alternative vapor-deposited organic coatings. For example, suitable poly(p-xylylene) polymer precursors can include different, or additional, halogen groups, or include reactive groups, such as amine groups, in various aspects. In addition to poly(chloro-p-xylylene) polymer, non-limiting examples of suitable poly(p-xylylene) polymers which can form a vapor-deposited organic coating can include poly(para-xylylene) polymer, poly(dichloro-p-xylylene) polymer, α-perfluorodi-p-xylene polymer, and poly(tetrafluoro-p-xylylene) polymer.

Alternatively, or additionally, further materials, such as additional polymers, can also be vapor-deposited simultaneously with, subsequently with, or prior to, the poly(p-xylylene) polymer precursor. For example, in certain aspects, one or more of tripropyleneglycol diacrylate ("TRPGDA") and hexanediol diacrylate ("HDODA") can be vapor-deposited with a poly(p-xylylene) polymer.

As can be further appreciated, additional chemical vapor deposition processes may also be suitable. For example, photochemical vapor deposition, initiated chemical vapor deposition, and aerosol assisted chemical vapor deposition may also be suitable processes to form a vapor-deposited organic coating in various aspects.

As can be appreciated, poly(p-xylylene) polymers can also, or alternatively, be commercially sourced in certain aspects. For example, suitable poly(p-xylylene) polymers marketed under the generic trade name "Parylene" can be used in certain aspects. As can be appreciated, poly(chloro-p-xylylene) polymer is Parylene C. Additional varieties of Parylene which can be vapor-deposited on a layer of water-soluble polymer as described herein include Parylene N (e.g., poly(para-xylylene) polymer), Parylene D (e.g., poly(dichloro-p-xylylene polymer), Parylene AF-4 (e.g., α-perfluorodi-p-xylene polymer), Parylene A (including one reactive amine group per repeat unit), Parylene AM (including one methylene amine group per repeat unit), and Parylene VT-4 (e.g., poly(tetrafluoro-p-xylylene) polymer).

Generally, the thickness of the vapor-deposited organic coating can be selected by controlling the amount of polymeric precursors introduced in the chemical vapor deposition process. In certain 5 aspects, the thickness of a poly(p-xylylene) polymer coating can be about 1 μm/g of poly(p-xylylene) polymer precursor.

In any of the various aspects described herein, the thickness of the vapor-deposited organic coating can be about 10 nanometers to about 1,000 nanometers, or about 100 nanometers to about 500 nanometers, about 200 nanometers to about 800 nanometers, or from about 250 nanometers to about 1,000 nanometers or from about 290 nanometers to about 500 nanometers, etc. As can be appreciated, the thickness of the vapor-deposited organic coating can influence the water-dispersibility with thinner coatings have a greater propensity for breaking into dispersible sizes.

In certain aspects, the vapor-deposited organic coating can be applied to less than substantially all of the water-soluble layer or backing layer. For example, the vapor-deposited organic coating can be applied to about 50% to about 100% of the water-soluble layer, or any integer percentage from about 50% to about 100% of the water-soluble layer, or any range formed by any of the preceding values such as about 60% or more, or about 95% or more of the water-soluble layer (or backing layer). In certain aspects, a mask can be used to apply the vapor-deposited organic coating to less than substantially all of the water-soluble layer or backing layer. As can be appreciated, other methods of reducing the coating area can also be used. For example, the water-soluble layer can be selectively modified to reduce adhesion of a vapor-deposited organic coating to select areas. In certain aspects, the vapor-deposited organic coating can be applied to substantially all of the water-soluble layer or backing layer.

As can be appreciated, other organic polymers can also be vapor-deposited on a water-soluble layer to form films with advantageous properties. For example, in certain aspects, the vapor-deposited organic coating can alternatively be formed of one or more of poly (carbonate urethane) urea ("PCUU"), poly (ester urethane) urea ("PEUU"), and poly (lactic-co-glycolic acid) ("PLGA"). In other embodiments, the vapor-deposited organic coating can be alternatively formed from one or more wax coatings such as paraffin, microcrystalline, petrolatum, vegetable-based, polyethylene based, and blends. Such organic polymers can also be applied to a water-soluble layer using chemical vapor deposition processes.

According to certain aspects, a vapor-deposited organic coating can be joined to a layer of water-soluble film zone either directly or indirectly. For example, in certain aspects, an organic vapor-depositing coating can be applied directly to an unprocessed water-soluble layer using a chemical vapor deposition process as previously described. As used herein, an unprocessed water-soluble layer refers to a layer which has not undergone any treatment steps, such as ablation, after being cast from a water-soluble polymeric material.

Alternatively, in certain aspects, a vapor-deposited organic coating can be applied to the water-soluble layer or backing layer after the layer has been prepared by, for example, cleaning. As can be appreciated, cleaning of the layer can promote improved adhesion of the vapor-deposited organic coating and can minimize any defects in the organic coating.

Generally, a water-soluble or backing layer can be cleaned in any suitable manner. For example, a layer can be cleaned with a solvent treatment or a physical abrasion treatment in certain aspects.

In certain aspects, the layer can be cleaned with an ablation process. In such aspects, one or more surfaces of the layer can be at least partially ablated to remove any undesirable material prior to application of the vapor-depositing organic coating. Additionally, certain ablation processes, such as plasma ablation processes, can also functionalize the surface and provide functional groups for the vapor-deposited organic coating to adhere to.

Generally, any suitable ablation process can be used including, for example, a plasma treatment, a solvent treatment, a flame treatment, a photon ablation treatment, an electron beam irradiation treatment, an ion bombardment treatment, an ultraviolet treatment, a vacuum annealing treatment, or a physical abrasion treatment. For example, a helium-oxygen plasma or an argon-oxygen plasma at a flow rate of 30.0 L/min at 100 W to about 150 W of power can be used to ablate the surface of a water-soluble layer prior to vapor deposition of an organic coating in certain aspects. Other gases can also be used for plasma ablation including nitrogen and ammonia. As can be appreciated, the surface of a water-soluble layer can be partially ablated, substantially fully ablated, or fully ablated in various aspects.

Alternatively, in certain aspects, the vapor-deposited organic coating can be applied over an intermediate layer. For example, a vapor-deposited organic coating can be applied to an indicia layer, or to a vapor-deposited inorganic coating in various aspects.

The product may comprise a vapor-deposited coating comprising poly(p-xylylene) polymer, for example wherein the poly(p-xylylene) polymer comprises one or more of poly(chloro-p-xylylene) polymer, poly(p-xylylene) polymer, poly(dichloro-p-xylylene) polymer, α-perfluorodi-p-xylene polymer, and poly(tetrafluoro-p-xylylene) polymer, and further wherein the poly(p-xylylene) polymer comprises poly(chloro-p-xylylene) polymer. These coatings impart a desirable shimmering or iridescent sheen to the product.

Inorganic Coating

In certain aspects, the films described herein can include a vapor-deposited inorganic coating as depicted in, for example, FIG. 2. Inclusion of a vapor-deposited inorganic coating can provide various improvements to a film. For example, a film including a vapor-deposited inorganic coating can further exhibit improved barrier properties and can obviate any need to clean the water-soluble layer or backing layer prior to application of the vapor-deposited organic coating.

In certain aspects, suitable vapor-deposited inorganic coatings can be formed of metal oxides. As used herein, metal oxides include aluminum oxides, magnesium oxides, titanium oxides, zinc oxides, as well as metalloid oxides such as silicon oxides. As can be appreciated, metal oxides can be vapor-deposited using a variety of processes. For example, a metal oxide layer can be vapor-deposited using a chemical vapor deposition process in certain aspects. Generally, most chemical vapor deposition processes are suitable due to the stability of the metal oxides and metal oxide precursors. Within these chemistries various stochiometries are possible and when we refer to an oxide we refer to any of the possible stochiometries, e.g. Al2O3 or AlOx etc.

In certain aspects, a plasma enhanced chemical vapor deposition can be used to form the vapor-deposited inorganic coating. Suitable precursor compounds which can be vaporized to form the inorganic layer can include, for example, tetramethylsilane ("TMS") and trimethylaluminum ("TMA"). TMS and TMA can respectively form silicon dioxide ("$SiO_2$") and aluminum oxide ("$Al_2O_3$") coatings. For example, a suitable TMS can be hexamethyldisiloxane ("HMDSO") in certain aspects. Power and flow rates can be determined based on variables such as the size of the substrate to be coated and the desired thickness of the vapor-deposited inorganic coating.

In certain aspects, an atomic layer chemical vapor deposition process can alternatively be used. Atomic layer deposition is a chemical vapor deposition process based on sequential, self-saturating surface reactions. In such processes, precursors are pulsed into a chemical vapor deposition chamber and allowed to build up layer by layer.

Alternatively, physical vapor deposition processes can be used in certain aspects. Physical vapor deposition processes differ from chemical vapor deposition processes by instead using physical processes such as heating or sputtering to produce vapor from a solid precursor. The vapor adsorbs onto the substrate to form a thin layer. In certain aspects, suitable physical vapor deposition processes to form an inorganic layer can include sputtering, such as magnetron sputtering, thermal evaporation, and e-beam evaporation.

It has been discovered that vapor-deposited inorganic coatings can exhibit a plurality of microfractures which develop under various circumstances such as the processing conditions used to handle the film and the thickness of the inorganic coating. In certain aspects, the vapor-deposited organic coating can overlay, and seal, the microfractures in the inorganic coating. For example, a vapor-deposited organic coating can cover a portion, substantially all, or all, of the microfractures present in the vapor-deposited inorganic coating. As can be appreciated, the vapor-deposited organic coating can be substantially, or entirely, free of microfractures.

In any of the various aspects described herein, the thickness of the vapor-deposited inorganic coating can be about 2 nanometers to about 1,000 nanometers, or from about 100 nanometers to about 500 nanometers, or about 100 nanometers to about 300 nanometers, etc.

In certain aspects, the vapor-deposited inorganic coating can be applied to less than substantially all of the water-soluble or backing layer. For example, the vapor-deposited inorganic coating can be applied to about 50% to about 100% of the layer, or about 60% to about 100%, or about 60% or more, or about 95% to about 100% of the layer. In certain aspects, a mask can be used to apply the vapor-deposited inorganic coating to less than substantially all of the layer. As can be appreciated, other methods of reducing the coating area can also be used. For example, the water-soluble layer can be selectively modified to reduce adhesion of a vapor-deposited inorganic coating to select areas. In certain aspects, the vapor-deposited inorganic coating can be applied to substantially all of the water-soluble or backing layer.

Barrier Patch

In an aspect, the barrier patch may comprise a backing layer having a first surface and a second surface and a WVTR from about 1 $g/m^2/24$ h to about 500 $g/m^2/24$ h; and a pressure sensitive adhesive zone, having a upper surface and a lower surface, and the pressure sensitive adhesive may be in contact with the first surface of the backing layer.

The backing layer may be a co-extruded film laminate comprising at least two layers, but can comprise 3, 4, 5, 6, or more layers. In an aspect, the backing layer or product or non-foamed first layer is substantially free of apertures.

"Apertures" as used herein means films having openings of a size and shape that allow for liquid molecules to pass through the film.

The barrier patch of the present invention may comprise a solid sheet material. The sheet provides the primary structure and shape to the product, allowing it to be handled and applied for treatment of a specific target area of the skin.

In certain aspects, backing layer is generally made of a flexible film material which is capable of remaining fitted and flexing during the movement of the human body and movements especially associated with facial expressions or gestures. By "flexible" it is meant that the product, barrier patch, and/or the backing layer may be substantially bent or folded without breaking, tearing, ripping, etc.

In an aspect, the product or barrier patch also does not collapse or fold under gravity or upon handling and application by the user. It is desirable for the product to conform to the target area of the skin surface to which it is applied without folding, crinkling, or inducing more wrinkling of the target area of the skin. Accordingly, the product or barrier patch is readily conformable to the skin and remains flexible throughout the duration of use, as the user moves during the period of time worn.

In certain aspects, a feature of the subject product is that the barrier patch, adhesive zone, and/or the backing layer are substantially free of, comprises only non-effective amounts of, or is free of or void of, a skin active agent. As such, the barrier patch, the adhesive zone, and/or the backing layer of the present invention may be characterized as a "blank" backing layer, adhesive zone, or barrier patch. In an aspect, an effective amount of the skin active agent employed in the product herein is substantially separate from the barrier patch, the adhesive zone, the vapor coating, and/or the backing layer. In an aspect, the pressure sensitive adhesive zone and water-soluble film zone are substantially separate. The term "substantially separate" as used herein means that one component is substantially free of the other component.

In one aspect, the backing layer may be a laminate comprising a film and a non-woven material for example, cotton, rayon, acrylic fibers, polypropylene fibers, polyester fibers and combinations, provided that the laminate comprises a WVTR from about 1 g/m²/24 h to about 500 g/m²/24 h.

The one or more layers of the barrier patch may comprise at least one material that includes but is not limited to polypropylene (PP); polyethylene (PE), metallocene plastomers, metallocene elastomers, high density polyethylene (HDPE), rubber modified LDPE, rubber modified LLDPE, acid copolymers, polysytyrene, cyclic polyolefins, polyethylene terephthalate (PET); polyvinylchloride (PVC); polyamide (PA); polycarbonate; polyurethane; cellulose acetate; polychloropene; polysulfone; polytetrafluoroethylene (PTFE); polyvinyl acetate (PVA); polyethylene glycol terephthalate film; polystyrene; polyphenylene oxide (PPO); acrylonitrile butadiene styrene (ABS); acrylic; acrylonitrile styrene acrylate (ASA); ethylene vinyl alcohol, natural rubber, latex, nylon, nitrile, silicone and thermo plastic elastomers (TPE), ethylene vinyl acetate (EVA), ethylene acrylic acid (EAA), copolymers of PE with PP, bimodal resins, any of which may be from either homopolymers or copolymers, and blends and combinations of these materials. Blends may be physical blends or reactor blends. The layers may comprise a single polymer or mixtures of polymers or copolymers. Laminates of these layer materials may also be used.

The backing layer(s) herein may comprise polyethylene. The term "polyethylene" or "PE" is used herein the broadest sense to include PE of any of a variety of resin grades, density, branching length, copolymer, blend, catalyst, and the like. The layer may comprise a blend of different grades of polyethylene, that may include LLDPE, LDPE, VLDPE, HDPE, or MDPE, or combinations thereof; manufactured using Ziegler-Natta catalysts, Chromium catalysts, metallocene based catalysts, single site catalysts, and other types of catalysts. The polymers may be homopolymers or copolymers. Blends may be physical blends or reactor blends. These materials can be bio-based, petro-based and recycled/reground. LLDPE copolymers can be made with any one or more of butene, hexene and octene comonomers. The ratio of the different grades can vary.

A preferred material for the one or more layers of the backing layer includes ethylene vinyl acetate, EVA (CAS No. 24937-78-8) copolymer. Different grades of EVAs tend to have different ethylene-to-vinyl acetate monomer ratios and/or different melt indices (molecular weights). For example, the percentage of VA monomer may range from about 20% to about 50% or from about 25% to about 40% of VA or from about 25% to about 30% of VA. For example, the melt flow index may range from about 0.7 dg/min to about 60 dg/min and/or from about 2 dg/min to about 6 dg/min and/or from about 2 dg/min to about 4 dg/min. EVA grades useful herein include Dupont Elvax® Grades: 260 (28% VA; Melt Flow Index MFI 6 dg/min via ASTM D1238); Grade 250 (28% VA; MFI 25 dg/min); Grade 150 and 150 W (32% VA; MFI 43 dg/min); Grade 40 W (40% VA; MFI 52 dg/min); and Celanese Ateva® 2803G (28% VA; MFI 3 dg/min via ASTM D1238) and Ateva® 1807EG (18% VA; MFI 0.7 dg/min).

Another preferred material for the backing layer or barrier patch is a polyethylene film sold under the tradename, 1525L, available from 3M, St. Paul, Minn. 3M 1525-L has a backing of polyethylene film of approximately 3 mil thickness, a 1.4 mil thick hypoallergenic, pressure sensitive acrylate adhesive layer and a paper release layer coated with polyethylene and silicone (3M 1525L may be used without the release layer).

A color masterbatch containing pigment and/or slip/antiblock agent and/or liquid colorants can also be added to the backing layer to afford certain aesthetics and functionality.

Pigments if present may typically be used in concentrations of about 0.5 wt. % to about 15 wt. %, and/or from about 1 wt. % to about 10 wt. %, or from 1.5 wt. % to about 7 wt. %, based on the total weight of the polymer (e.g. of the backing layer).

Other additives are further detailed in U.S. patent publications including U.S. patent application Ser. No. 13/924,983, filed Jun. 24, 2013 (P&G US 2014/0376835; Case 12966Q); and U.S. patent application Ser. No. 13/924,999, filed Jun. 24, 2013 (P&G Case 12967Q), and the references cited therein.

For example the backing layer of the barrier patch optionally can include an additive such as a slip agent or an antistatic agent (e.g., euracamide, a steramide), a filler (e.g., talc, clay, pulp, titanium dioxide, thermoplastic starch, raw starch wood flour, diatomaceous earth, silica, inorganic glass, inorganic salts, pulverized plasticizer, pulverized rubber), a pigment (e.g., mica, titania, carbon black), a UV inhibitor, an anti-coloring agent, a mold release agent, a flame retardant, an electrically conductive agent, an antioxidant, an impact modifier, a stabilizer (e.g., a UV absorber), wetting agents, carbon, graphene and a biodegradable-enhancing additive (e.g., an oxo-degradable additive or an organic material). An oxo-degradable additive is often compounded into a polymer in a concentration of about 1 wt. % to about 5 wt. %, based on the total weight of the polymer, and includes at least one transition metal that can foster oxidation and chain scission in plastics when exposed to heat, air, light, or mixtures thereof. Organic materials (e.g., cellulose, starch, ethylene vinyl acetate, and polyvinyl alcohol) also can be used as biodegradable-enhancing additives, although they cannot promote degradation of the non-degradable portion of the polymer matrix.

In a preferred aspect, the multi-layered co-extruded backing layer has at least three layers, and is preferably an ethylene vinyl acetate ("EVA") comprising film. In a preferred aspect, a foamed layer is in-between layers of non-foamed layers, e.g. the non-foamed first layer and the non-foamed third layer, on either side.

In one aspect, the barrier patch comprises a backing layer comprising:
(i) a non-foamed first layer comprising a non-foamed polymer film having a first surface;
(ii) a foamed second layer comprising a foamed polymer film; 73%, and a thickness of from 10 microns to 250 microns, preferably from 40 microns to 160 microns.

In an aspect, the backing layer of the barrier patch comprises three layers, e.g. a foamed second layer optionally comprising EVA and a layer of non-foamed EVA on either side, i.e., a first non-foamed EVA layer and a third non-foamed EVA layer wherein the foamed EVA layer is in-between said first and third non-foamed layers.

In one aspect, the multi-layer barrier patch and/or the backing layer is substantially free of fiber, nanofibers, or non-woven material for example, cotton, rayon, acrylic fibers, polypropylene fibers, polyester fibers.

In another aspect, the barrier patch and/or backing layer includes a corona treatment. For example, the backing layer or barrier patch may be additionally treated, for example by corona discharge or coating with an adhesion promoter which as a primer may effect anchoring of the active and adhesive.

The material composition and/or polymer resins used in the foamed layer may be different from those used in the non-foamed layer(s), since the material composition and/or resins may be optimized for foam formation, or other film layer properties. Additives, particularly small amount of nucleating agents selected from the group consisting of $CaCO_3$, clays, talcs, and combinations thereof, may be included for quick bubble formation during foaming process.

Pressure Sensitive Adhesive Zone

The barrier patch may comprise a backing layer and pressure sensitive adhesive zone. Typically, the pressure sensitive adhesive zone comprises a pressure-sensitive adhesive (PSA) that is suitable for long-term skin contact, and which should be physically and chemically compatible with the backing layer and/or additives that are present. Examples of suitable adhesive materials include, but are not limited to, the following: acrylic and methacrylic ester homo- or copolymers, butyl rubber based systems, silicones, urethanes, vinyl esters and amides, olefin copolymer materials, natural or synthetic rubbers, hot-melt adhesives (see, for example, U.S. Pat. No. 5,387,450); polyethylenes; polysiloxanes; polyisobutylenes; polyacrylates; polyacrylamides; polyurethanes; plasticized ethylene-vinyl acetate copolymers; and tacky rubbers such as polyisobutene, polybutadiene, polystyrene-isoprene copolymers, polystyrene-butadiene copolymers, and neoprene (polychloroprene) and combinations thereof.

According to one aspect the adhesive is a hotmelt adhesive including adhesives selected from the group consisting of ethyl vinyl acetate, metallocene polyalphaolefins, polyolefins including atactic polyalphaolefins, block copolymers such as diblocks copolymers and triblock copolymers, polyurethane hot melts, polyamides and combinations thereof. In one aspect, the adhesive comprises a combination of diblock copolymers and triblock copolymers. Diblocks and triblock copolymers may include styrene/isoprene; styrene/butadiene; butylene/ethylene/styrene; and combinations thereof.

High viscosity triblock copolymers may be used as adhesives and have the configuration A-B-A wherein the polymer blocks A are non-elastomeric polymer blocks which, as homopolymers have glass transition temperatures above 20° C. The elastomeric polymer blocks, B, are generally isoprene or butadiene which may be partially or substantially hydrogenated or mixtures thereof. Further, the copolymers may be linear or branched.

Diblock copolymers may generally have the A-B configuration where A and B are as described previously.

Liquid diluents may be added to the adhesive compositions. The adhesive composition may comprise from about 60% to about 99% diluents, by weight. In an aspect, the majority of the liquid diluent is oil. Preferably the liquid diluent comprises, or consists essentially of, oils such as highly refined white petroleum mineral oil. Useful diluents are primarily aliphatic in character and compatible with the polymer midblock. Plasticizers may also be included, e.g. paraffinic and naphthenic petroleum oils, highly refined aromatic-free paraffinic and naphthenic food and technical grade oils, highly refined white petroleum mineral oils, and liquid tackifiers such as the synthetic liquid oligomers of polybutene, polypropene, polyterpene, etc. The synthetic process oils may be high viscosity oligomers which may be permanently fluid/liquid monoolefins, isoparaffins or paraffins of moderate to high molecular weight.

In an aspect, the adhesive is selected from the TECHNOMELT® and DERMA-TAK® brands available from Henkel, for example TECHNOMELT PSM 154A DERMA-TAK®. DERMA-TAK products are pressure-sensitive adhesives and encompass both solvent-based acrylic and formulated rubber (liquid and hotmelt) pressure-sensitive adhesives. Useful adhesives may also be selected from those described in U.S. Pat. Nos. 6,448,303 and 5,559,165.

In an aspect, the pressure sensitive adhesive zones are continuous, discontinuous, or a combination thereof. The product may also comprise a plurality of discontinuous adhesive zones.

Thickness

In one aspect, the overall total thickness of the barrier patch or the product is from about 20 microns to about 500 microns, preferably from about 50 microns to about 200 microns, more preferably from about 70 to about 180 microns, yet more preferably from about 75 microns to about 150 microns and combinations thereof.

In another aspect, the water-soluble film zone (dry state) has a total thickness of about 2 microns to about 200 microns, preferably from 50 microns to about 175 microns, more preferably from about 75 to about 170 microns. In an aspect, the water-soluble film zone in the dry state, has a thickness of about 5 microns to about 50 microns, or about 15 microns to about 30 microns.

In an aspect, the pressure sensitive adhesive zones typically have an average thickness ranging from about 5 microns to about 350 microns, in alternative aspects about 10 microns to about 120 microns.

In an aspect, the typical basis weight for the product herein ranges from about 40 to about 190 gsm, for instance about 45 gsm to about 170 gsm and/or from about 50 gsm to about 140 gsm.

Continuous or Discontinuous Zones

The pressure sensitive adhesive zone and the water-soluble film zone may be continuous or discontinuous such that they comprise continuous or discontinuous patterns. In an aspect, the adhesive zone and the soluble film zone may both be continuous. In some aspects, a portion of the adhesive zone and the soluble film zone are continuous and another portion may be discontinuous. By applying the soluble film zone and the adhesive zone to the vapor coating or backing layer in a discontinuous pattern, a portion of the skin-facing surface of the product and the adhesive zone remains exposed to the skin to permit sufficient adhesion, via the pressure sensitive adhesive, to the skin. In one aspect, the soluble film zone should be applied to the adhesive zone so that it covers about 1% to about 99% of the skin facing surface area of the adhesive zone or product, or about 10% to about 90%, and/or about 20% to about 80% of the skin facing surface area of the adhesive zone or the product.

In one aspect, the pressure sensitive adhesive zone is applied to the vapor coating or backing layer in a pattern to define a pattern of discontinuous adhesive free areas and the soluble film zone is applied to the adhesive free areas of the vapor coating or backing layer. In another aspect, the pressure sensitive adhesive zone is applied to the vapor coating or backing layer in a series of rows or stripes to define a pattern of adjacent adhesive free areas that are stripes or rows, and the soluble film zone is applied to the adhesive free areas/stripes of the vapor coating or backing layer.

The soluble film zone may be applied to the adhesive zone or the backing layer or the vapor coating in a regular pattern, a random pattern, and combinations thereof. For example, the soluble film zone may be configured in either a regular or random pattern of elements such as straight lines, angled lines, curved lines, intersecting lines, dots, circles and geometric shapes, amorphous shaped, etc. or a combination of these elements.

Size and Shape of Product

The product may have a size and shape adapted to conform to a desired target area of skin which could be a human face or part thereof, legs, hands, arms, feet, or human torso. They are generally flat in appearance.

The exact size and shape of the product will depend upon the intended use and product characteristics. The product herein can be, for example, a square, circle, semicircle, rectangle, triangle, oval, ring, crescent, crescent with rounded corners, teardrop or other more complex and irregular shape. The shape of the product may be selected from the group consisting of circle, square, rectangle, triangle, and/or irregular shape that conforms to the contours of the forehead, perioral, and/or periorbital areas of the human face.

In certain other aspects, the product comprises a size and shape to treat different areas of the face such as the forehead, the under-eye area and the under-eye area combined with the crow's feet area around the eye. Thus, the size of the product may be determined by the size of the target area of skin to be treated. Thus, a product is shaped to fit the face or the target area of skin the surface area may range from about 0.25 cm$^2$ to about 50 cm$^2$, and/or from about 1 cm$^2$ to about 30 cm$^2$, and/or from about 1 cm$^2$ to about 20 cm$^2$, and/or from about 1 cm$^2$ to about 15 cm$^2$, and/or from about 5 cm$^2$ to about 15 cm$^2$. Surface area refers to that of a flat plane having the same boundary as the surface i.e. ignoring any surface texturing present.

WVTR

According to one aspect, the vapor coating and backing layer together (or either the vapor coating or backing layer or product) have an WTVR value between about 1 g/m$^2$/24 h to about 500 g/m$^2$/24 h. and in another aspect, has a WVTR from about 1 g/m$^2$/24 h to about 250 g/m$^2$/24 h and/or from about 1 g/m$^2$/24 h to about 180 g/m$^2$/24 h and/or from about 2 g/m$^2$/24 h to about 150 g/m$^2$/24 h and/or from about 2 to about 20 g/m$^2$/24 h. The term WTVR stands for "Water Vapor Transmission Rate", i.e. the amount of vapor which can pass per unit area during a certain period of time.

The vapor coating and/or backing layer in certain aspects are non-porous or water impermeable. In certain other aspects, they are impermeable to the cosmetic composition, the soluble film zone, the skin care active agent employed, and fluids wherein the WVTR is from about from about 2 to about 100 g/m$^2$/24 h. While not being bound by theory this minimizes water loss from the soluble film or cosmetic composition while in contact with the keratinous tissue and skin, prevents the water-soluble film zone or cosmetic composition, once hydrated, from drying out. This drying out may result in reduced or loss of efficacy and/or irritation to the skin.

Such relative water impermeability and lower water vapor permeability may increase the effectiveness and efficiency of the cosmetic composition. For example, without being bound by theory, the relative water impermeability and lower vapor permeability employed may serve to enhance or increase the penetration of the skin care active agent into the skin.

In certain aspects, the backing layer may, for example, consist of a perforated polyolefin film, where the size of the holes has been chosen so that air and vapor may pass, but not liquid molecules. One example of such film is described in U.S. Pat. No. 5,628,737 and/or micro-porous plastic films, as is described in, for example. EP-A-0238200. These laminates and films, when coated with the vapor coating go from a higher WVTR and higher levels of breathability to a lower WVTR.

Release Layer

The product herein may further optionally comprise a protective release layer removably attached to the consumer facing side of the pressure sensitive adhesive or the soluble film zone of the product. The release layer provides protection for the pressure sensitive adhesive zone and/or the soluble film zone from the environment and prior to application by the user.

The protective release layer may comprise materials including polymer resins such as a polyolefins e.g. polypropylene (including stratified biaxially oriented polypropylene (SBOPP)), polyethylene (including LDPE; LLDPE; HDPE; Metallocene) or polyethylene terephthalate, polyesters, and combinations thereof. Alternative materials which may be used include polyvinylchloride, polyamide, acetyl, acrylonitrile butadiene styrene, acrylic, acrylonitrile styrene acrylate, ethylene vinyl alcohol, ethylene vinyl acetate, Nylon, Latex, natural or synthetic rubbers, polycarbonate, polystyrene, silicone or thermo plastic elastomer, thermo plastic vulcanate or copolymers of said materials, and combinations thereof. Where appropriate the protective release layer may comprise one or more laminations, combinations of multiple layers. In an aspect, the protective release layer may comprise a coating of a non-stick material. Exemplary non-stick coatings include wax, silicone, fluoropolymers such as TEFLON®, and fluorosilicones.

In an aspect, the protective release layer covers the entire aforementioned area of pressure sensitive adhesive zone coating the barrier patch. In another aspect, the protective release layer is water impermeable. In a further aspect, the release layer has a mean thickness of at least about 50 microns, or at least about 85 microns, or from about 50 microns to about 150 microns, and/or from about 90 microns to about 120 microns.

The release layer may optionally extend, in whole or part, beyond the pressure sensitive adhesive zone to provide a removal tab that facilitates ease of removal of the release layer.

Cosmetic Composition

Skin Active Agents

In one aspect, the product provides an effective amount of a skin active agent to be delivered to the target area of skin. In another aspect, the product provides from about 0.5 mg/cm2 to about 3 mg/cm2 of the cosmetic composition, and/or from about 1 mg/cm2 to about 2 mg/cm2 to the target area of skin. In one aspect and without being bound by theory, the use of the proper amount of the cosmetic composition will minimize the interaction of the cosmetic composition with the pressure sensitive adhesive. The compositions of the present invention may comprise a skin active agent which provides a skin care benefit characteristic of the usage of the skin care product. The skin care benefit may include benefits related to appearance or make-up of the skin. The skin care active can provide acute (immediate and short lived) benefits, or chronic (long term and longer lasting) benefits.

The term "skin active agent" as used herein, means an active ingredient which provides a cosmetic and/or therapeutic effect to the area of application on the skin. The skin active agents useful herein include skin lightening agents, anti-acne agents, emollients, non-steroidal anti-inflammatory agents, topical anesthetics, artificial tanning agents, anti-microbial and anti-fungal actives, skin soothing agents, sun screening agents, skin barrier repair agents, anti-wrinkle agents, anti-skin atrophy actives, lipids, sebum inhibitors, sebum inhibitors, skin sensates, protease inhibitors, anti-itch agents, desquamation enzyme enhancers, anti-glycation agents, diaper rash agents, anti-eczema agents, botanicals, and mixtures thereof. When included, the present composition comprises a safe and effective amount of a skin active agent and/or from about 0.0001% to about 20%, in another aspect from about 0.01% to about 10% of at least one skin active agent.

The cosmetic compositions may include from about 0.00001 to about 10% by weight of botanical actives or from about 0.01 to about 8 percent by weight, or from about 0.05 to about 5 percent by weight. "Botanical" herein means a substance, extract or derivative of a plant and may also be described as "herbals". Botanicals may include water-soluble or oil-soluble active materials extracted from a particular plant including materials extracted from echinacea, yucca glauca, willow herb, basil leaves. Turkish oregano, carrot root, grapefruit fruit, fennel fruit, rosemary, thyme, blueberry, bell pepper, black tea, blackberry, black currant fruit, Chinese tea, coffee seed, dandelion root, date palm fruit, gingko leaf, green tea polyphenols (e.g. epicatechin gallate and epigallocatechin 3-O-gallate), hawthorn berries, licorice, oolong tea, sage, strawberry, sweet pea, tomato, vanilla fruit, neohesperidin, quercetin, rutin, morin, myricetin, chlorogenic acid, glutathione, glycyrrhizin, absinthe, arnica, centella asiatica, chamomelle, comfrey, cornflower, horse chestnut, ivy (Herdera helix), magnolia, mimosa, oat extract, pansey, scullcap, seabuckthorn, white nettle, witch hazel and any combinations thereof.

The type and amount of skin active agents are selected so that the inclusion of a specific agent does not affect the stability of the composition. For example, hydrophilic agents may be incorporated in an amount soluble in the aqueous phase, while lipophilic agents may be incorporated in an amount soluble in the oil phase.

Other skin active agents purported to exhibit expression-line relaxing benefits for use in the present invention include, but are not limited to, Lavandox available from Barnet Products Corporation; Thallasine 2, available from BiotechMarine; Argireline NP, available from Lipotec; Gatuline In-Tense and Gatuline Expression, available from Gattefosse; Myoxinol LS 9736 from BASF Chemical Company, Syn-ake, available from DSM Nutritional Products, Inc.; and Instensyl®, available from Silab, Inc; Sesaflash™ available from Seppic Inc.

Skin lightening agents useful herein refer to active ingredients that improve hyperpigmentation as compared to pre-treatment. Useful skin lightening agents herein include ascorbic acid compounds, vitamin $B_3$ compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents is believed to be advantageous in that they may provide skin lightening benefit through different mechanisms.

Ascorbic acid compounds useful herein include ascorbic acid per se in the L-form, ascorbic acid salt, and derivatives thereof. Ascorbic acid salts useful herein include, sodium, potassium, lithium, calcium, magnesium, barium, ammonium and protamine salts. Ascorbic acid derivatives useful herein include, for example, esters of ascorbic acid, and ester salts of ascorbic acid. Particularly preferred ascorbic acid compounds include 2-o-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. Commercially available ascorbic compounds include magnesium ascorbyl phosphate available from Showa Denko, 2-o-D-glucopyranosyl-L-ascorbic acid available from Hayashibara and sodium L-ascorbyl phosphate with tradename STAY C available from Roche.

Vitamin $B_3$ compounds useful herein include, for example, those having the formula:

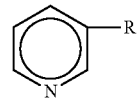

wherein R is —$CONH_2$ (e.g., niacinamide) or —$CH_2OH$ (e.g., nicotinyl alcohol); derivatives thereof; and salts thereof. Exemplary derivatives of the foregoing vitamin $B_3$ compounds include nicotinic acid esters, including non-vasodilating esters of nicotinic acid, nicotinyl amino acids, nicotinyl alcohol esters of carboxylic acids, nicotinic acid N-oxide and niacinamide N-oxide. Preferred vitamin $B_3$ compounds are niacinamide and tocopherol nicotinate, and in another aspect, is niacinamide. In a preferred aspect, the vitamin $B_3$ compound contains a limited amount of the salt form and is more preferably substantially free of salts of a vitamin $B_3$ compound. Preferably the vitamin $B_3$ compound contains less than about 50% of such salt, and is more preferably substantially free of the salt form. Commercially available vitamin $B_3$ compounds that are highly useful herein include niacinamide USP available from Reilly.

Other hydrophobic skin lightening agents useful herein include ascorbic acid derivatives such as ascorbyl tetraisopalmitate (for example, VC-IP available from Nikko Chemical), ascorbyl palmitate (for example available from Roche Vitamins), ascorbyl dipalmitate (for example, NIKKOL CP available from Nikko Chemical); undecylenoyl phenyl alanine (for example, SEPIWHITE MSH available from Seppic); octadecenedioic acid (for example, ARLATONE DIOIC DCA available from Uniquema); *Oenothera biennis* sead extract, and pyrus malus (apple) fruit extract, Water and Myritol 318 and butylene glycol and tocopherol and sscorbil tetraisopalmitate and Paraben and Carbopol 980 and DNA/SMARTVECTOR UV available from COLETICA, magnesium ascorbyl phosphate in hyaluronic filling sphere available from COLETICA, and mixtures thereof.

Other skin active agents useful herein include those selected from the group consisting of N-acetyl D-glucosamine, panthenol (e.g., DL panthenol available from Alps Pharmaceutical Inc.), tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate: DL-α-tocopheryl acetate available from Eisai), azelaic acid, arachidonic acid, tetracycline, ibuprofen, naproxen, ketoprofen, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

The compositions of the present invention in various aspects may comprise N-acyl amino acid compounds. Suitable N-acyl amino acid compounds include, but are not limited to, N-acyl phenylalanine. N-acyl tyrosine, their isomers, including their D and L isomers, salts, derivatives, and mixtures thereof. An example of a suitable N-acyl amino acid is N-undecylenoyl-L-phenylalanine is commercially available under the tradename SEPIWHITE (Registered trademark) from Seppic (France).

Skin care agents are also disclosed in US Publication No. 2007/0020220A1, published Jan. 25, 2007, wherein the components/ingredients are incorporated herein by reference in their entirety.

The cosmetic composition may comprise one or more peptides. Herein, "peptide" refers to peptides containing ten or fewer amino acids, their derivatives, isomers, and complexes with other species such as metal ions (for example, copper, zinc, manganese, and magnesium). As used herein, peptide also refers to both naturally occurring and synthesized peptides. In one aspect, the peptides are di-, tri-, tetra-, penta-, and hexa-peptides, their salts, isomers, derivatives, and mixtures thereof. Examples of useful peptide derivatives include, but are not limited to, peptides derived from soy proteins, palmitoyl-lysine-threonine (pal-KT) and palmitoyl-lysine-threonine-threonine-lysine-serine (pal-KTTKS, available in a composition known as MATRIXYL®) palmitoyl-glycine-glutamine-proline-arginine (pal-GQPR, available in a composition known as RIGIN®), these three being available from Sederma, France. and Cu-histidine-glycine-glycine (Cu-HGG, also known as IAMIN®). In various aspects, the cosmetic composition may comprise from about $1 \times 10^{-7}\%$ to about 20%, alternatively from about $1 \times 10^{-6}\%$ to about 10%, and alternatively from about $1 \times 10^{-5}\%$ to about 5% of the peptide.

In one aspect, the skin active agent is niacinamide. In one aspect, the agent is a combination of niacinamide, glycerine, tocopherol acetate, and D-panthenol. Niacinamide may be included in the composition in an amount between about 1% to about 30 wt %, in another aspect from about 2% to about 28 wt %, in another aspect from about 5% to about 25 wt %, and in another aspect from about 10% to about 20 wt %. When D-panthenol is included, it may be present in an amount of about 0.5% to about 5 wt %, or about 0.5% to about 3 wt % and/or about 0.5% to about 2 wt %. Glycerin may be included as an active in an amount from about 6% to about 20 wt %, and/or from about 8% to about 15 wt %, and/or from about 10% to about 15 wt %.

In various aspects, the skin active agent is selected from niacinamide, alone or in combination with one or more of palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, tretinoin, and combinations thereof.

In an aspect, the cosmetic compositions herein may be aqueous solutions, or emulsions such as oil-in-water emulsions, water-in-oil emulsions or multiple emulsions having aqueous or oily external phases. In another aspect, the cosmetic compositions herein are oil-in-water emulsions.

In one aspect to avoid a negative interaction with the pressure sensitive adhesive, the cosmetic composition or water-soluble film zone comprises only low levels of silicones of about 0.5% to about 10%, and/or from about 1% to about 5% and/or the cosmetic composition is substantially free of silicones. As used herein "silicones" may refer to those silicones disclosed in US 2007/0020220A1, published Jan. 25, 2007, Osborne, for example in paragraphs [0226] to [0258].

In one aspect, the cosmetic composition is substantially free of depilatory agents.

The cosmetic composition or water-soluble film zone may comprise an effective amount of a skin active agent having activity to improve visual or aesthetic appearance of the skin, such as an agent effective to reduce or diminish the appearance of fine lines and/or wrinkles on human facial skin or an agent effective to treating existing acne lesions, reducing redness associated with acne lesions and/or protecting from formation of acne lesions.

In another aspect, a method of treating skin is provided, comprising applying the product to a target area of the skin, comprising an effective amount of a skin active agent.

The methods of treatment, application, regulation, or improvement disclosed herein may utilize the product and/or multi-layered barrier patch. Application of the present product can occur on any target area of skin surface of the body. Skin surfaces of the most concern tend to be those not typically covered by clothing such as facial skin surfaces, hand and arm skin surfaces, foot and leg skin surfaces, and neck and chest skin surfaces (e.g., décolletage). Application may be on a facial skin surface including the forehead, perioral, chin, periorbital, nose, and/or cheek skin surfaces.

The step of applying the product to a target area of skin may be done by localized application to the target area, for example an area that contains wrinkles. In reference to the application, the term "localized", "local", or "locally" mean that it is delivered to the target area of skin (such as an area of skin containing wrinkles) while minimizing delivery to skin surface not requiring treatment.

One or more products of the present invention can be applied broadly to one or more facial skin surfaces to reduce the appearance of wrinkles within those facial skin regions.

The method of treating skin herein may optionally begin with a cleansing step. The consumer can wash his or her face with a suitable cleanser (e.g., Olay Purifying Mud Lathering Cleanser, available from The Procter & Gamble Company, Cincinnati, Ohio), and gently dry his or her skin.

The product may be applied to at least one target portion of skin selected from the group consisting of a forehead, perioral, chin, periorbital, nose, cheek, skin surface, and combinations thereof. The product may be applied to the target portion of skin for a treatment period. The treatment period may comprise at least once a day for at least four weeks, preferably applied at least twice a day for at least four weeks, more preferably at least once a day for at least eight weeks, and more preferably at least twice a day for at least eight weeks, preferably the length of the treatment period is at least 2 weeks, preferably at least 4 weeks, and more preferably at least 8 weeks. The product may remain on the target portion of skin for about 1 minute to about 24 hours or from about 2 hours to about 10 hours, prior to the removal from the skin. In an aspect, the target portion of skin comprises a hyperpigmented spot, wrinkles, fine lines, dryness, skin laxity and combinations thereof.

Test Methods

Water Vapor Transmission Rate (WVTR) for Soluble Films (Coated & Un-Coated)

The Water Vapor Transmission Rate Test Method a water soluble film plus a vapor deposited coating is performed according to the following. The specimens are tested according to ASTM F-1249-13, under the following test conditions: temperature of 40° C. (+/−0.56° C.) and relative humidity of 50% (+/−3%). The water vapor transmission rate is measured in (or converted to) units of $g/(m^2 \cdot day)$. For materials outside of the Scope (§ 1.1) of ASTM F-1249-13, the Water Vapor Transmission Rate Test Method does not apply.

Water Vapor Transmission Rate (WVTR) for Backing Layer (Coated & Un-Coated)

WVTR of the vapor coating and/or backing layer is measured according to ASTM F1249-13 at 37° C. (+/−0.56° C.) and 35% RH (+/−3%), unless otherwise indicated herein. Samples may be analyzed on a MOCON Permatran-W 3/33 Water Vapor Permeability Instrument using ASTM F1249. The water vapor transmission rate is measured in (or converted to) units of $g/(m^2 \cdot day)$. For samples with higher WVTR (e.g. from approximately 300 $g/m^2/24$ h to 500 $g/m^2/24$ h) samples may be analyzed per ASTM E-96 with desiccant placed inside the test cups and 35% RH surrounding the exterior of the cups. Samples of barrier patches are prepared and do not include the pressure sensitive adhesive.

Basis Weight

Basis Weight is calculated as follows. Sample Preparation: Samples were equilibrated at TAPPI conditions for 100 hours (50% RH, 23° C.). Cut samples to 25.4 mm wide strips using JDC 1" strip cutter. Cut samples to 80 mm long using gage block. Weigh each sample using 4 place analytical balance. Basis weight is calculated as the sample mass/area, where mass is measured on the balance and area=25.4 mm×80 mm=2032 mm=0.002032 meters. Basis weight is reported in units of grams/meter$^2$.

Thickness Measurements

Inorganic Coating Thickness:

In order to determine the thickness of inorganic coatings, an INFICON XTC/3 Thin Film Deposition Controller is used in situ (within the vacuum chamber) during deposition.

Organic Coating Thickness:

In order to measure the thickness of the organic coatings put down under certain conditions, a strip of Kapton tape is placed over a cleaned silicon wafer. The wafer is then coated with organic material at the same time that the soluble film sample is coated. The tape is then removed from the silicon wafer, and the thickness of the coated wafer is measured using a KLA Tencor P-15 Profilometer.

Product Thickness:

Thickness measurement may be performed using ASTM D5729 which typically uses a pad caliper with a known pressure (0.1 psi) and a gage sensor. A Qualitest Thickness Tester, Model CHY-C2, available from www.WorldofTest.com may be used.

Oxygen Transmission Rate Test

The Oxygen Transmission Rate Test Method for a film is performed according to the following. The specimens are tested according to ASTM F-1927-14, under the following test conditions: temperature of 37° C. (+/−0.5° C.), relative humidity of 35% (+/−3%), wherein the oxygen partial pressure on the test gas side is equal to the oxygen partial pressure on the carrier gas side (both being the ambient pressure). The oxygen transmission rate is measured in (or converted to) units of $cm^3/(m^2$ day). For materials outside of the Scope (§ 1.1) of ASTM F-1927-14, the Oxygen Transmission Rate Test Method does not apply.

Dissolution Method

The water-soluble film is aged for 24 hours at 21° C. (+/−1.5° C.) and 50% relative humidity (+1-1.5% relative humidity). Cut three test specimens of the water-soluble film sample to a size of 3.8 cm×3.2 cm. Lock each specimen in a separate 35 mm slide mount. Fill a suitable beaker with 500 mL of distilled water, and maintain a constant temperature of 20° C. Mark height of column of water. Place beaker on magnetic stirrer, add magnetic stirring rod to beaker, turn on stirrer, and adjust stir speed until a vortex develops which is approximately one-fifth the height of the water column. Mark depth of vortex. Secure the 35 mm slide mount in an alligator clamp of a slide mount holder such that the long end of the slide mount is parallel to the water surface. The depth adjuster of the holder should be set so that when dropped, the end of the clamp will be 0.6 cm below the surface of the water. One of the short sides of the slide mount should be next to the side of the beaker with the other positioned directly over the center of the stirring rod such that the film surface is perpendicular to the flow of the water. In one motion, drop the secured slide and clamp into the water and start the timer. When all visible film is released from the slide mount, raise the slide out of the water while continuing to monitor the solution for undissolved film fragments. For each sample, record the time when all film fragments of each sample are no longer visible to the naked eye, and the solution becomes clear. Average the time values for the 3 samples and if the average time is 15 minutes or less, then the sample constitutes a water-soluble film.

Alternative Procedure to Analyze Coating Thickness

In order to measure the thickness of a vapor deposited coating on a film, high resolution Scanning Electron Microscopy (SEM) may be used. In order to prepare a sample for thickness measurements, cut the sample in half in order to obtain a cross-section, using a microtome, preferably a cryogenic microtome in order to get the best cut without smearing the surface to be examined. This assumes that the film is already clean. However if the film is part of a commercial consumer product e.g. such as a Beauty Care product, then cut a smaller sample of the product and clean. Cleaning can be achieved by carefully wiping any product off the inside of the film that had been directly in contact with the product. Cleaning would be conducted using a soft paper tissue until any visible product has been removed. Dust and dirt from particles can be removed from the other surface using an air gun. Then place the sample on a vertical stub using double sided carbon tape to hold the sample in place. Then sputter coat the sample with Au—Pd prior to SEM, to ensure a good image. The cross-sectional area of the sample would then be examined to determine if a coating was present on either of the film surfaces—and if present, note the thickness by looking at the scale on the SEM.

EXAMPLES

Example 1

Table 1 further evaluates the water vapor transmission rates of various soluble films. The 76 micron films of Table 1 were evaluated in accordance to that described in the test method section for soluble films.

TABLE 1

| Examples | Water Vapor Transmission Rate g/(m² · day) |
|---|---|
| Comparative Example 1 - Uncoated PVOH 1 | 233 [15.0] (Avg. of 2 samples) |
| Inventive Example 2 - Ex. 1 + 300 nm poly(chloro-p-xylylene) polymer coating | 82.6 [5.33] (Avg. of 2 samples) |
| Inventive Example 3 - Ex. 1 + 1,000 nm Al₂O₃ coating + 300 nm poly(chloro-p-xylylene) polymer coating | 23.9 [1.54] |
| Inventive Example 4 - Ex. 1 + 300 nm Al₂O₃ coating + 300 nm poly(chloro-p-xylylene) polymer coating | 92.8 [5.99] |
| Inventive Example 5 - Ex. 1 + 100 nm Al₂O₃ coating + 300 nm poly(chloro-p-xylylene) polymer coating | 36.1 [2.33] (Avg. of 2 samples) |
| Inventive Example 6 - Ex. 1 + SiO$_x$ + 300 nm poly(chloro-p-xylylene) polymer coating | 82.5 [5.32] |
| Inventive Example 7 - Ex. 1 + 1000 nm Al2O3 | 120.9 [8.06] |

As illustrated in Table 1, each film including a vapor-deposited coating demonstrated reduced water vapor transmission rates compared to the uncoated films described in the Comparative Example. An example coated with 1000 nm of Al$_2$O$_3$ with no organic coating is also shown for comparison.

TABLE 2

| Examples | Water Vapor Transmission Rate g/(m² · day) |
|---|---|
| Comparative Example 8 - Uncoated EVA film (160 microns) | 66 (Avg. of 2 samples) |
| Inventive Example 9 - Ex. 9 + 300 nm poly(chloro-p-xylylene) polymer coating | 33.1 (Avg. of 2 samples) |

As illustrated in Table 2, the film including a vapor-deposited organic coating demonstrated reduced water vapor transmission rates compared to the uncoated films described in the Comparative Example. Typically to half the WVTR without the coating, the thickness of the film would have to increase to about 320 μm to achieve the same or similar result. Thicker films are generally less comfortable to wear on the skin and may cause the adhesive to detach from the skin. In addition the poly(p-xylylene) polymer coating such as poly(chloro-p-xylylene) polymer provides mild iridescence effect and is transparent. Thus it allows the porous nature of the underlying backing layer such as foamed EVA to be observed.

TABLE 3

| Examples | Oxygen Transmission Rate cc/(m² · day) |
|---|---|
| Comparative Example 10 - Uncoated EVA film (160 microns) | 33,650 (Avg. of 2 samples) |
| Inventive Example 11 - Ex. 10 + 300 nm poly(chloro-p-xylylene) polymer coating | 7,250 (Avg. of 2 samples) |

As illustrated in Table 3, the film including a vapor-deposited organic coating demonstrated reduced oxygen transmission rates compared to the uncoated films described in the Comparative Example.

Example 2

The following are non-limiting examples of products and methods of the present invention. The examples are given solely for illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified. The listed formulations may comprise the listed components and any minor materials associated with such components. As is apparent to one of ordinary skill in the art, the selection of these minors will vary depending on the physical and chemical characteristics of the ingredients selected to make the present invention as described herein.

A. Preparation of Beauty Care Product:

| | Component | Weight % |
|---|---|---|
| Solution A | PEG 100 Stearate (surfactant) | 1% |
| | Emulgade PL 68-50[1] (surfactant) | 1% |
| | Eutanol G 16[2] (hexyldecanol) | 10% |
| Solution B | Sepiwhite MSH (Undecylenoyl phenylalanine)[3] | 0.4% |
| | 1N Sodium Hydroxide solution | 1.26% |
| Solution C | Water | 52.34% |
| | Niaciniamide | 10% |
| | Glycerol | 20% |
| | Inositol | 4% |

[1]Available from BASF.
[2]Available from BASF.
[3]Available from BASF.

Mix the ingredients of Solution A and heat to 80° C. with stirring. Then place Solution B ingredients into a small beaker and stir until the solution becomes clear to deprotonate the Sepiwhite MSH to make it soluble in water. Then heat ingredients of Solution C to 80° C. with stirring.

Add Solution B slowly to Solution C with rapid stirring for 10 minutes. Then add Solution A slowly over 15 minutes with rapid stirring at 80° C. and stir for 30 minutes and then mill with a hand-held mill for 2 minutes at 80° C. Stir the solution and allow to cool to RT. Once at RT, place the solution into a jar and label. After 96 hours, the solution is stable with no separation and no solids forming.

Once the above emulsions are obtained, mix a 60:40 ratio (of water soluble polymer solution to emulsion). The water-soluble polymer solution is Methocel E5LV at a 20% solution in water. Then cast a film with the use of a Gardo Draw Down table and a #44 Draw Down bar, onto a transfer sheet. Alternatively, the film may be printed via a screen printing method onto the transfer sheet. Methocel E5LV is a water-soluble cellulose ether of low viscosity available from Dow/Coloron LTD.

Coating

The film is then coated with the coating that was used and described in Inventive Example 5 (100 nm $Al_2O_3$ coating + 300 nm poly(chloro-p-xylylene) polymer coating).

First, directly vaporize the $Al_2O_3$ of the final coating, formed on the surface of a water-soluble layer by sputtering, or e-beam evaporation, of solid aluminum oxide pellets or granules. An example of a device that can be used for this process is a Temescal FC 1800 E-beam Evaporator and in this device the distance between the target and substrate is about 45 cm, the energy of the electron beam is 450 W (using 950 KV at 50 uA) and before beginning deposition, the chamber is pumped down to a vacuum level of about $1 \times 10^{-5}$ Torr.

The sample is then removed from this first chamber and placed in a different system to form the poly(chloro-p-xylylene) coating on top of the Al2O3 coating. There are several stages to forming the poly(chloro-p-xylylene) coating, inside a sealed system that has multiple tubes and chambers that allow gas to flow from the vaporizer section, through the pyrolysis zone, into the deposition chamber, past the probe cold trap and then through the vacuum pump, which exhausts to atmosphere. First the solid dichloro-di(p-xylylene) dimer is vaporized/sublimed at a temperature of 150° C. under a pressure of 13.3 Pa (0.1 torr) inside the vaporizer tube. The dimer gas then flows (under the pumping action of the vacuum pump) through the pyrolysis zone (a high temperature tube furnace) and is pyrolyzed at 690° C. and 66.7 Pa (0.5 torr) which causes the dimer gas to be cleaved to form chloro-p-xylylene gas. This gas then flows into the chemical vapor deposition chamber which contains the film substrate—this chamber is held at a temperature of about 25° C. and a pressure of 6.7 Pa (0.05 torr), though the pressure does rise slightly by about 15-30 milliTorr as the dimer gas flows into it, until the vaporization step is complete. Within this deposition chamber, the chloro-p-xylylene gas condenses and polymerizes to form a coating of poly (chloro-p-xylylene) on the surface of the inorganic coating. Once deposition to the desired thickness is complete, the chamber can be brought up to atmospheric pressure and the film substrate can be removed.

In another aspect the inorganic coating may be eliminated and the organic coating (300 nm of poly(chloro-p-xylylene) may be coated on the surface of the water soluble layer. If this is done, the film can be first be ablated to maximize adhesion to the film substrate. Ablation can be achieved using a helium-oxygen plasma or an argon-oxygen plasma at a flow rate of 30.0 L/min at 100 W to about 150 W of power.

Product with Backing and Adhesive Layer

A backing layer according to Sample 3 of Provisional U.S. Patent Application Ser. No. 62/257,341, filed on Nov. 19, 2015, is provided. In particular Sample 3 is a 3-layer film having a foamed core layer and non-foamed outer layers. All layers are made of EVA. The outside layers each have approximately 20 µm thickness and the core foamed layer has approximately 130 µm thickness. The total thickness of the backing layer is approximately 170 µm. The basis weight is about 99 gsm and the WVTR is 82 $g/m^2/24$ hours. The backing layer has a first surface. Alternatively, the backing layer may comprise a low-density polyethylene film or a non-foamed laminate of EVA. The backing layer or barrier patch may also comprise a polyethylene film sold under the tradename. 3M 1525L, available from 3M. St. Paul, Minn., (without the release layer) which has a backing of polyethylene film of approximately 3 mil thickness and a 1.4 mil thick hypoallergenic, pressure sensitive acrylate adhesive layer.

Slot coat a pressure sensitive adhesive (if an adhesive is not already present with the backing layer), such as for example, TECHNOMELT® and DERMA-TAK® brands available from Henkel, (for example TECHNOMELT PSM 154A DERMA-TAK®) at a basis weight of about 50 $g/m^2$ to about 160 $g/m^2$ or specifically about 95 $g/m^2$, on the first surface of the backing layer. Slot coat the pressure sensitive adhesive as a continuous layer across the first surface of the backing layer.

After the coating of pressure sensitive adhesive is complete, the upper surface of the pressure sensitive adhesive layer/zone is coated with the above soluble film comprising the skin active agent by contacting the soluble film side of the transfer sheet to the upper surface of pressure sensitive adhesive. The soluble film is coated as a discontinuous layer on the upper (outer) surface of the pressure sensitive adhesive layer/zone. The soluble film has a coating basis weight from about 30 $g/m^2$ to about 200 $g/m^2$.

The assembly of the barrier patch may also be accomplished by the methods described in US Ser. Nos. 62/257,341; 62/257,347 and 62/257,351, assignee Procter & Gamble, each filed on Nov. 19, 2015.

Then coat either the organic vapor coating alone or with the inorganic vapor coating to the backing layer on the side opposite to the water-soluble layer, via the coating method described in this section.

Exemplary products, for example the Product of the above example, for treatment of periorbital skin aging are attached, via the adhesive side, to periorbital area. The Product is applied and worn for an extended period of approximately 7-8 hours such as overnight, and thereafter removed. The Products herein deliver an effective amount of the skin active agent in a manner that achieves penetration of the skin active agent into the stratum corneum, and/or other layers of the epidermis, and in many aspects, into the basal skin layer and/or dermis.

ADDITIONAL EXAMPLES

A. A multi-layered beauty care product for applying a skin active agent to the skin, comprising:
   a layer of a water-soluble film zone comprising:
     a top surface and a bottom surface;
     a water-soluble film forming polymer;
     a cosmetic composition comprising an effective amount of a skin active agent; and
   a vapor-deposited coating, wherein the vapor-deposited coating is selected from the group consisting of a vapor-deposited organic coating comprising poly(p-xylylene) polymer, a metal oxide inorganic coating, and combinations thereof.

B. The product of paragraph A wherein the vapor-deposited coating substantially consists of or consists of the poly(p-xylylene) polymer.

C. The product of any of any preceding paragraph wherein the poly(p-xylylene) polymer comprises one or more of poly(chloro-p-xylylene) polymer, poly(p-xylylene) polymer, poly(dichloro-p-xylylene) polymer, α-perfluorodi-p-xylene polymer, and poly(tetrafluoro-p-xylylene) polymer.

D. The product of any of any preceding paragraph, wherein the poly(p-xylylene) polymer comprises poly(chloro-p-xylylene) polymer.

E. The product of any of any preceding paragraph, wherein the vapor-deposited coating is directly applied to only one surface of the layer of water-soluble film zone.

F. The product of any preceding paragraph, wherein the surface of the layer of water-soluble film zone is at least partially ablated or is substantially fully ablated, with a treatment selected from the group consisting of a plasma treatment, a solvent treatment, a flame treatment, a photon ablation treatment, an electron beam irradiation treatment, an ion bombardment treatment, an ultraviolet treatment, a vacuum annealing treatment, a physical abrasion treatment, and combinations thereof.

G. The product of any preceding paragraph, wherein the layer of water-soluble film zone is ablated with a helium-oxygen plasma or an argon-oxygen plasma.

H. The product of any preceding paragraph wherein the water-soluble film zone comprises from about 30% to about 99%, preferably from about 40% to about 90%, more preferably from about 50% to about 75% of the water-soluble film forming polymer, wherein preferably the water-soluble film forming polymer is selected from the group consisting of polyethylene oxide polymer, polyvinyl alcohols, polyvinyl alcohol copolymers, starch, methylcellulose, carboxymethylcellulose sodium, hydroxyethyl cellulose, hydroxypropyl methylcellulose and combinations, preferably the water-soluble film forming polymer is a methylcellulose, polyethylene oxide polymer and combinations thereof.

I. The product of any preceding paragraph wherein the water-soluble film forming polymer is selected from the group consisting of polyethylene oxide having a molecular weight from about 500 to about 10,000,000, preferably from about 10,000 to about 1,000,000, more preferably from about 100,000 to about 300,000 or from about 150,000 to about 250,000.

J. The product of any preceding paragraph wherein the layer of water-soluble film zone further comprises one or more plasticizers, gas-barrier additives, and bittering agents.

K. The product of paragraph J wherein the water-soluble film zone further comprises from about 2% to about 80% by weight, of a plasticizer, preferably from about 2% to about 60% and wherein the plasticizer is selected from the group consisting of glycerol, ethylene glycol, diethyleneglycol, propylene glycol, sorbitol, pentaerythritol, glucamine, N-methylglucamine, sodiumcumenesulfonate and mixtures thereof, preferably the plasticizer is glycerol.

L. The product of any preceding paragraph comprising a plurality of layers of water-soluble film zone.

M. The product of any preceding paragraph wherein the vapor-deposited coating has a thickness of about 10 nanometers to about 1,000 nanometers, preferably a thickness of about 100 nanometers to about 500 nanometers.

N. The product of any preceding paragraph wherein the water-soluble film zone has a total thickness of about 5 microns to about 150 microns, preferably from 10 microns to about 120 microns, more preferably from about 15 to about 60 microns.

O. The product of any preceding paragraph wherein the product has a total thickness of 5 microns to 500 microns, preferably from 20 microns to 200 microns, more preferably from 70 to 180 microns.

P. The product of any preceding paragraph wherein the vapor-deposited coating is joined to about 60% to about 100% of at least one of the surfaces of the water-soluble film zone.

Q. The product of any preceding paragraph comprising a vapor-deposited inorganic coating and a vapor-deposited organic coating, wherein the vapor-deposited inorganic coating is joined to the vapor-deposited organic coating.

R. The product of any preceding paragraph wherein the metal oxide is selected from the group consisting of aluminum oxide, silicon oxide, magnesium oxide, titanium oxide, and combinations thereof.

S. The product of paragraph Q or R wherein the vapor-deposited organic coating is directly applied to the vapor-deposited inorganic coating.

T. The product of any preceding paragraph wherein the vapor-deposited inorganic coating has a thickness of about 10 nanometers to about 2,000 nanometers, preferably a thickness of about 100 nanometers to about 500 nanometers.

U. The product of any preceding paragraph wherein the product further comprises a pressure sensitive adhesive zone, having an upper surface and a lower surface, the lower surface of the pressure sensitive adhesive zone in contact with the surface of the layer of water-soluble film zone that is opposite to the vapor-deposited coating.

V. The product of paragraph U wherein the pressure sensitive adhesive zone is selected from the group consisting of acrylic and methacrylic ester homo- or copolymers, butyl rubber based systems, silicones, urethanes, vinyl esters and amides, olefin copolymer materials, and combinations thereof.

W. The product of paragraph U or V wherein the water-soluble film zone and the adhesive zone are substantially separate.

X. The product of paragraph U. V or W wherein the adhesive zone and the soluble film zone are continuous, discontinuous, or a combination thereof.

Y. The product of paragraph U, V, W or X wherein the adhesive zone is substantially free of a skin active agent.

Z. The product of any preceding paragraph further comprising:
  a backing layer having a first surface and a second surface;
  a pressure sensitive adhesive zone, having an upper surface and a lower surface, the lower surface of the pressure sensitive adhesive zone in contact with the first surface of the backing layer;
  the water-soluble film zone is in contact with either the first surface of the backing layer, the upper surface of the adhesive zone, or both; and
  the vapor coating is in contact with the second surface of the backing layer.

AA. The product of any preceding paragraph comprising a WVTR from about 1 g/m$^2$/24 h to about 500 g/m$^2$/24 h, preferably about 1 g/m$^2$/24 h to about 250 g/m$^2$/24 h. more preferably from about 2 g/m$^2$/24 h to about 20 g/m$^2$/24 h.

BB. The product of paragraph Z or AA wherein the backing layer is a laminate comprising a film and a non-woven material.

CC. The product of paragraph Z or AA wherein the product or backing layer is substantially free of fibrous absorbent materials, superabsorbent materials, non-woven materials, cotton, rayon, acrylics, polypropylene fibers and polyester fibers.

DD. The product of any preceding paragraph wherein the composition comprises from about 0.01% to about 10% of a skin active agent selected from the group consisting of vitamin E, vitamin A, vitamin B, palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, tretinoin, botanicals, and combinations thereof, preferably the skin active agent comprises niacinamide, glycerine, tocopherol acetate, D-panthenol, and combinations thereof.

EE. The product of paragraph Q, R, S or T wherein the vapor-deposited organic coating is substantially free from microfractures and covers a portion or substantially all of the plurality of microfractures present in the vapor-deposited inorganic coating.

FF. The product of any predeing paragraph further comprising:
- a backing layer having a first surface and a second surface;
- a pressure sensitive adhesive zone, having an upper surface and a lower surface, the lower surface of the pressure sensitive adhesive zone in contact with the first surface of the backing layer;
- the vapor deposited coating is in contact with the upper surface of the adhesive;
- the water-soluble film zone is in contact with the vapor deposited coating.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While aspects of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A multi-layered beauty care product for applying a skin active agent to skin, comprising:
   a discontinuous water soluble film layer comprising:
      a plurality of discrete water soluble film zones spatially separated from one another,
      a water soluble film forming polymer comprising a polyethylene oxide polymer and about 2% to about 80% of a plasticizer, and
      a cosmetic composition comprising an oil-in-water or water-in oil-emulsion and an effective amount of a skin active agent;
   a vapor deposition layer comprising a vapor-deposited organic coating layer and optionally a vapor-deposited inorganic metal oxide layer, wherein the vapor-deposited organic coating layer comprises a poly(p-xylylene) polymer; and
   a pressure sensitive adhesive layer positioned between the discontinuous water soluble film layer and the vapor deposition layer, wherein the plurality of discrete water soluble film zones are spatially separated from one another by the pressure sensitive adhesive layer;
   wherein the product has a water vapor transmission rate (WVTR) of about 1 g/m$^2$/24 h to about 500 g/m$^2$/24 h.

2. The product of claim 1, wherein the poly(p-xylylene) polymer comprises one or more of poly(chloro-p-xylylene) polymer, poly(p-xylylene) polymer, poly(dichloro-p-xylylene) polymer, α-perfluorodi-p-xylene polymer, and poly(tetrafluoro-p-xylylene) polymer.

3. The product of claim 2, wherein the poly(p-xylylene) polymer comprises poly(chloro-p-xylylene) polymer.

4. The product of claim 1, wherein the vapor-deposited coating is directly applied to only one surface of the layer of water-soluble film zone.

5. The product of claim 1, wherein the surface of the layer of water-soluble film zone is at least partially ablated or is substantially fully ablated, with a treatment selected from the group consisting of a plasma treatment, a solvent treatment, a flame treatment, a photon ablation treatment, an electron beam irradiation treatment, an ion bombardment treatment, an ultraviolet treatment, a vacuum annealing treatment, a physical abrasion treatment, and combinations thereof.

6. The product of claim 1, wherein the layer of water-soluble film zone is ablated with a helium-oxygen plasma or an argon-oxygen plasma.

7. The product of claim 1 wherein the water-soluble film zone comprises about 30% to about 99% of the water-soluble film forming polymer, wherein the water-soluble film forming polymer is selected from the group consisting of polyethylene oxide polymer, polyvinyl alcohols, polyvinyl alcohol copolymers, starch, methylcellulose, carboxymethylcellulose sodium, hydroxyethyl cellulose, hydroxypropyl methylcellulose and combinations thereof.

8. The product of claim 7 wherein the water-soluble film zone is a water-soluble film forming polymer selected from the group consisting of polyethylene oxide having a molecular weight from about 500 g/mol to about 10,000,000 g/mol.

9. The product of claim 1 wherein the layer of water-soluble film zone further comprises one or more gas-barrier additives, and bittering agents.

10. The product of claim 9 wherein the plasticizer is selected from the group consisting of glycerol, ethylene glycol, diethyleneglycol, propylene glycol, sorbitol, pentaerythritol, glucamine, N-methylglucamine, sodiumcumenesulfonate and mixtures thereof.

11. The product of claim 1 comprising a plurality of layers of water-soluble film zone.

12. The product of claim 1 wherein the vapor-deposited coating has a thickness of about 10 nanometers to about 1,000 nanometers.

13. The product of claim 1 wherein the water-soluble film zone has a total thickness of about 5 microns to about 150 microns.

14. The product of claim 1 wherein the product has a total thickness of 5 microns to 500 microns.

15. The product of claim 1, wherein the vapor-deposition layer comprises the vapor-deposited organic coating layer and the vapor-deposited inorganic coating layer, and wherein the vapor-deposited inorganic coating layer is joined to the vapor-deposited organic coating layer.

16. The product of claim 1 wherein the metal oxide is selected from the group consisting of aluminum oxide, silicon oxide, magnesium oxide, titanium oxide, and combinations thereof.

17. The product of claim 15 wherein the vapor-deposited organic coating is directly applied to the vapor-deposited inorganic coating.

18. The product of claim 1 wherein the vapor-deposited inorganic coating has a thickness of about 10 nanometers to about 2,000 nanometers.

19. The product of claim 1, wherein the pressure sensitive adhesive is selected from the group consisting of acrylic and methacrylic ester homo- or copolymers, butyl rubber based systems, silicones, urethanes, vinyl esters and amides, olefin copolymer materials, and combinations thereof.

20. The product of claim 1, wherein the adhesive zone is substantially free of a skin active agent.

21. The product of claim 1, further comprising:
a backing layer having a first surface and a second surface, wherein the pressure-sensitive adhesive layer is positioned between the backing layer and the water-soluble film layer and the backing layer is positioned between the pressure-sensitive adhesive layer and the vapor deposition layer.

22. The product of claim 21 wherein the backing layer is a laminate comprising a film and a non-woven material.

23. The product of claim 21 wherein the product or backing layer is substantially free of fibrous absorbent materials, superabsorbent materials, non-woven materials, cotton, rayon, acrylics, polypropylene fibers and polyester fibers.

24. The product of claim 1, wherein the composition comprises from about 0.01% to about 10% of a skin active agent selected from the group consisting of vitamin E, vitamin A, vitamin B, palmitoyl-lysine-threonine, palmitoyl-lysine-threonine-threonine-lysine-serine, N-undecyl-10-enoyl-L-phenylalanine, retinyl propionate, N-acetyl glucosamine, vitamin C, tretinoin, salicylic acid, benzoic acid, benzoyl peroxide, tretinoin, botanicals, and combinations thereof.

25. The product of claim 15 wherein the vapor-deposited organic coating layer is substantially free from microfractures and covers a portion or substantially all of the plurality of microfractures present in the vapor-deposited inorganic metal oxide layer.

* * * * *